United States Patent
Bunnage et al.

(10) Patent No.: US 6,670,366 B1
(45) Date of Patent: Dec. 30, 2003

(54) PYRAZOLOPYRIMIDINONE CGMP PDE5 INHIBITORS FOR THE TREATMENT OF SEXUAL DYSFUNCTION

(75) Inventors: Mark Edward Bunnage, Sandwich (GB); John Paul Mathias, Sandwich (GB); Stephen Derek Albert Street, Sandwich (GB); Anthony Wood, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/426,552

(22) Filed: Oct. 22, 1999

(30) Foreign Application Priority Data

Oct. 23, 1998 (GB) .............................................. 9823101

(51) Int. Cl.$^7$ .................... C07D 487/04; C07D 401/12; C07D 231/40; A61K 31/519; A61P 15/10
(52) U.S. Cl. ................................ 514/262.1; 514/234.2; 544/118; 544/262; 546/293; 548/364.1; 548/372.5
(58) Field of Search ..................... 540/575; 546/247, 546/193, 293; 514/218, 234.2, 262.1; 544/118, 256, 262; 548/364.1, 372.5

(56) References Cited

U.S. PATENT DOCUMENTS

| | | | |
|---|---|---|---|
| 4,663,326 A | 5/1987 | Hamilton | 514/258 |
| 4,666,908 A | 5/1987 | Hamilton | 514/229 |
| 5,250,534 A | 10/1993 | Bell et al. | 514/258 |
| 5,272,147 A | 12/1993 | Bell et al. | 514/234.2 |
| 5,346,901 A | 9/1994 | Bell et al. | 514/258 |
| 5,426,107 A | 6/1995 | Bell et al. | 514/234.2 |
| 5,719,283 A | 2/1998 | Bell et al. | 544/262 |
| 5,734,053 A | 3/1998 | Terrett | 544/277 |
| 5,736,548 A | 4/1998 | Bacon et al. | 514/258 |
| 5,955,611 A | 9/1999 | Dunn et al. | 544/262 |

FOREIGN PATENT DOCUMENTS

| | | | |
|---|---|---|---|
| EP | 0210188 | 2/1987 | ............ H01R/43/20 |
| EP | 0463756 | 1/1992 | ......... C07D/487/04 |
| EP | 0349239 | 3/1994 | ......... C07D/487/04 |
| EP | 0636626 | 2/1995 | ......... C07D/487/04 |
| EP | 0526004 | 8/1997 | ......... C07D/487/04 |
| WO | WO9306104 | 4/1993 | ......... C07D/487/04 |
| WO | WO9307149 | 4/1993 | ......... C07D/487/04 |
| WO | WO9312095 | 6/1993 | ......... C07D/239/91 |
| WO | WO9400453 | 1/1994 | ......... C07D/473/30 |
| WO | WO9405661 | 3/1994 | ......... C07D/471/04 |
| WO | WO9428902 | 12/1994 | ......... A61K/31/505 |
| WO | WO9616644 | 6/1996 | ......... A61K/31/00 |
| WO | WO9616657 | 6/1996 | ......... A61K/31/505 |
| WO | WO9628429 | 9/1996 | ......... C07D/239/70 |
| WO | WO9628448 | 9/1996 | ......... C07D/487/04 |
| WO | 9849166 A1 * | 11/1998 | |
| WO | WO9849166 | 11/1998 | ......... C07D/487/04 |
| WO | 9954333 A1 * | 10/1999 | |
| WO | WO9954333 | 10/1999 | |

OTHER PUBLICATIONS

Streitwieser, A. and Heathcock, C.H., "Introduction to Organic Chemistry, 2nd Ed.", Macmillan, New York, 1981, p. 40.*
John D. Roberts and Marjorie C. Caserio, "Basic Principles of Organic Chemistry", Benjamin, New York, 1964, p. 63.*
63 USPQ 19 (1944).*
Maw, G.N. Annual Reports Med. Chem., vol. 34, 1999, pp. 71–80.*
"The Condensed Chemical Dictionary, Ninth Ed." Gesser G. Hawley, Van Nostrand, New York, 1977, pp. 27 and 650.*
DuMaitre et al., J. Med. Chem., 39(8), 1996, 1635–1644.
J. Med. Chem., 1996, 39, 1635.
Abstract 08253484.
Harriet W. Hamilton, et al., J. Med. Chem. 1987, 30, pp. 96–96.

* cited by examiner

Primary Examiner—Richard L. Raymond
Assistant Examiner—Tom McKenzie
(74) Attorney, Agent, or Firm—Peter C. Richardson; Gregg C. Benson; James T. Jones

(57) ABSTRACT

There is provided compounds of formula IA and of formula IB,

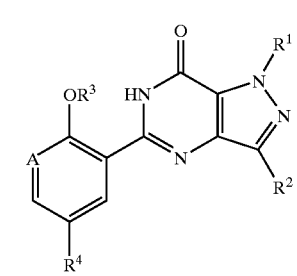

IA

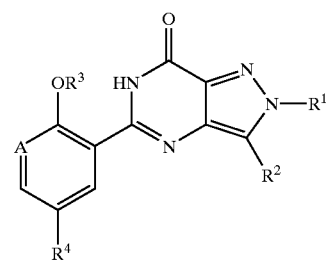

IB wherein $R^1$, $R^2$, $R^3$, $R^4$ and A have meanings given in the description, which are useful in the curative and prophylactic treatment of a medical condition for which inhibition of a cyclic guanosine 3',5'-monophosphate phosphodiesterase (e.g. cGMP PDE5) is desired.

13 Claims, No Drawings

PYRAZOLOPYRIMIDINONE CGMP PDE5 INHIBITORS FOR THE TREATMENT OF SEXUAL DYSFUNCTION

FIELD OF THE INVENTION

This invention relates to pharmaceutically useful compounds, in particular compounds which are useful in the inhibition of cyclic guanosine 3', 5'-monophosphate phosphodiesterases (cGMP PDEs), such as type 5 cyclic guanosine 3', 5'-monophosphate phosphodiesterases (cGMP PDE5). The compounds therefore have utility in a variety of therapeutic areas, including male erectile dysfunction (MED).

PRIOR ART

International patent application WO 94/28902 discloses the use of certain pyrazolopyrimidinone compounds in the treatment of impotence.

DISCLOSURE OF THE INVENTION

According to a first aspect of the invention there is provided compounds of formulae IA and IB:

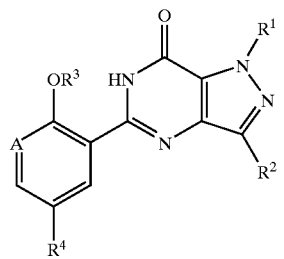

IA

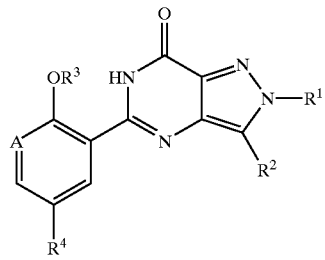

IB wherein

A represents CH or N;

R1 represents Het$^1$, Het$^1$alkyl, aryl or arylalkyl, all of which are optionally substituted by one or more substituents selected from halo, cyano, nitro, lower alkyl, OR$^5$, C(O)R$^6$, C(O)OR$^7$, C(O)NR$^8$R$^9$, NR$^{10a}$R$^{10b}$ and SO$_2$NR$^{11a}$R$^{11b}$;

R$^2$ and R$^3$ independently represent H or lower alkyl, which latter group is optionally substituted and/or terminated by one or more substituents selected from aryl, Het$^1$, halo, cyano, nitro, OR$^5$, C(O)R$^6$, C(O)OR$^7$, C(O)NR$^8$R$^9$, NR$^{10a}$R$^{10b}$ and SO$_2$NR$^{11a}$R$^{11b}$;

R$^4$ represents SO$_2$NR$^{12}$R$^{13}$;

R$^{12}$ and R$^{13}$ independently represent H; lower alkyl optionally substituted and/or terminated by one or more substituents selected from aryl, Het$^1$, halo, cyano, nitro, lower alkyl, OR$^5$, C(O)R$^6$, C(O)OR$^7$, C(O)NR$^8$R$^9$, NR$^{10}$R$^{10a}$ and SO$_2$NR$^{11a}$R$^{11b}$; Het$^1$; or together with the nitrogen to which they are attached, form Het$^2$ or structural fragment of formula IIa:

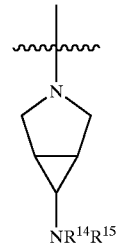

IIa

R$^{14}$ and R$^{15}$ independently represent H, lower alkyl, C(O)R$^6$, C(O)OR$^7$ or C(O)NR$^8$R$^9$;

Het$^1$ represents an optionally substituted four- to twelve-membered heterocyclic group, which group contains at least one nitrogen atom and, optionally, one or more further heteroatoms selected from nitrogen, oxygen and sulphur;

Het$^2$ represents an optionally substituted three- to twelve-membered heterocyclic group, which group contains at least one nitrogen atom and, optionally, one or more further heteroatoms selected from nitrogen, oxygen and sulphur; and R$^5$, R$^6$, R$^7$, R$^8$, R$^9$, R$^{10a}$, R$^{10b}$, R$^{11a}$ and R$^{11b}$ independently represent, at each occurrence when used herein, H or lower alkyl;

or a pharmaceutically, or a veterinarily, acceptable derivative thereof;

provided that when R$^2$ represents C$_{1-6}$ alkyl and:

(a) A represents CH; R$^1$ represents Het$^1$ or Het$^1$CH$_2$ (in which both cases Het$^1$ represents a C-linked 6-membered heterocyclic group containing one or two nitrogen atoms, optionally in the form of its mono-N-oxide, or a C-linked 5-membered heterocyclic group containing from one to four heteroatoms selected from nitrogen, oxygen and sulphur, wherein either of said heterocyclic groups is optionally substituted with one or two substituents selected from C$_{1-4}$ alkyl, which alkyl group is optionally substituted with C$_{1-4}$ alkoxy, halo or NH$_2$), phenyl or benzyl (which latter two groups are optionally substituted with one or two substituents selected from C$_{1-4}$ alkyl, C$_{1-4}$ alkoxy, halo, CN, CONH$_2$, NO$_2$, NH$_2$ and SO$_2$NH$_2$); and R$^3$ is C$_{1-6}$ alkyl optionally substituted with C$_{1-4}$ alkoxy; then R$^{12}$ and R$^{13}$ do not represent, together with the nitrogen atom to which they are attached, a piperazinyl group, optionally substituted in the 4(N) position with C$_{1-4}$ alkyl optionally substituted with OH, C$_{1-4}$ alkoxy or CONH$_2$; and (b) A represents N; R$^1$ represents CH$_2$Het$^1$(in which Het$^1$ represents a C-linked 6-membered heterocyclic group containing one or two nitrogen atoms, optionally in the form of its mono-N-oxide, or a C-linked 5-membered heterocyclic group containing two or three nitrogen atoms, wherein either of said heterocyclic groups is optionally substituted with C$_{1-4}$ alkyl) or benzyl; and R$^3$ is C$_{1-4}$ alkyl (optionally substituted with one or two substituents selected from OH, C$_{1-4}$ alkoxy, benzyloxy, NR$^{5a}$R$^{6a}$ (where R$^{5a}$and R$^{6a}$are each independently selected from H and C$_{1-4}$ alkyl or, together with the nitrogen atom to which they are attached, form a pyrrollidinyl, piperidinyl or morpholinyl group), phenyl, furanyl or pyridinyl), C$_{3-6}$ cycloalkyl or 1-(C$_{1-4}$alkyl)

piperidinyl; then $R^{12}$ and $R^{13}$ do not represent, together with the nitrogen atom to which they are attached, a 4-piperazinyl group, optionally substituted with one or two $C_{1-4}$ alkyl groups, optionally in the form of its 4-N-oxide, and optionally substituted at the 4(N) position with $C_{1-4}$ alkyl optionally substituted with one or two substituents selected from OH, $NR^{5a}R^{6a}$, $CONR^{5a}R^{6a}$ (in which both cases $R^{5a}$ and $R^{6a}$ are as defined above);

which compounds are referred to together hereinafter as "the compounds of the invention".

The term "aryl", when used herein, includes six- to ten-membered carbocyclic aromatic groups, such as phenyl and naphthyl. Each "aryl" group identified herein is optionally substituted with one or more substituents selected from halo, cyano, nitro, $OR^5$, $C(O)R^6$, $C(O)OR^7$, $C(O)NR^8R^9$, $NR^{10a}R^{10b}$, $SO_2NR^{11a}R^{11b}$, $N(H)SO_2R^{11a}$ and lower alkyl, which latter group is optionally substituted and/or terminated by one or more substituents selected from halo, cyano, nitro, lower alkyl, $OR^5$, $C(O)R^6$, $C(O)OR^7$, $C(O)NR^8R^9$, $NR^{10a}R^{10b}$, $SO_2NR^{11a}R^{11b}$ and $N(H)SO_2R^{11a}$.

The term "Het$^1$", when used herein, includes four- to twelve-membered, preferably four- to ten-membered, ring systems, which may be aromatic in character. Each "Het$^1$" group identified herein is optionally substituted with one or more substituents selected from halo, cyano, nitro, $OR^5$, $C(O)R^6$, $C(O)OR^7$, $C(O)NR^8R^9$, $NR^{10a}R^{10b}$, $SO_2NR^{11a}R^{11b}$, $N(H)SO_2R^{11a}$ and lower alkyl, which latter group is optionally substituted and/or terminated by one or more substituents selected from halo, cyano, nitro, lower alkyl, $OR^5$, $C(O)R^6$, $C(O)OR^7$, $C(O)NR^8R^9$, $NR^{10a}R^{10b}$, $SO_2NR^{11a}R^{11b}$ and $N(H)SO_2R^{11a}$. The term "Het$^1$" thus includes groups such as optionally substituted azetidinyl, pyrrolidinyl, imidazolyl, indolyl, oxadiazolyl, thiadiazolyl, triazolyl, tetrazolyl, oxatriazolyl, thiatriazolyl, pyridazinyl, morpholinyl, pyrimidinyl, pyrazinyl, pyridinyl, quinolinyl, isoquinolinyl, piperidinyl, pyrazolyl, imidazopyridinyl and piperazinyl.

The term "Het$^2$", when used herein, includes three- to twelve-membered, preferably four- to ten-membered, ring systems, which may be aromatic in character. Each "Het$^2$" group identified herein is optionally substituted with one or more substituents selected from oxo, ethyleneketal, halo, cyano, nitro, $OR^5$, $C(O)R^6$, $C(O)OR^7$, $C(O)NR^8R^9$, $NR^{10a}R^{10b}$, $SO_2NR^{11a}R^{11b}$, $N(H)SO_2R^{11a}$ and lower alkyl, which latter group is optionally substituted and/or terminated by one or more substituents selected from halo, cyano, nitro, lower alkyl, $OR^5$, $C(O)R^6$, $C(O)OR^7$, $C(O)NR^8R^9$, $NR^{10a}R^{10b}$, $SO_2NR^{11a}R^{11b}$ and $N(H)SO_2R^{11a}$. The term thus includes groups such as imidazolyl, indolyl, oxadiazolyl, thiadiazolyl, triazolyl, tetrazolyl, oxatriazolyl, thiatriazolyl, pyridazinyl, pyrimidinyl, pyrazinyl, pyridinyl, quinolinyl, isoquinolinyl, morpholinyl, tetrahydrothiazinyl, pyrazolyl, imidazopyridinyl and aza- and diaza-cyclo-$(C_2–C_{12})$-alkyl groups, such as aziridinyl, azetidinyl, pyrrolidinyl, piperidinyl, piperazinyl, aza- or diazacycloheptyl, -cyclooctyl, -cyclononyl, -cyclodecyl, -cycloundecyl and -cyclododecyl.

All Het$^1$ and Het$^2$ groups may also be in the form of an N-oxide.

For the avoidance of doubt, when $R^{12}$ and $R^{13}$ together represent Het$^2$, the nitrogen atom to which they are attached is the nitrogen atom that must be present in this ring.

"The term "lower alkyl", when used herein, includes C1–6 alkyl. Lower alkyl lower alkenyl, lower alkynyl, cyclic lower alkyl, part cyclic/acyclic lower alkyl groups which $R^2$, $R^3$, $R^5$, $R^6$, $R^7$, $R^8$, $R^9$, $R^{10a}$, $R^{10b}$, $R^{11a}$, $R^{11b}$, $R^{12}$, $R^{13}$, $R^{14}$ and $R^{15}$ may represent, and with which $R^1$, $R^{12}$, $R^{13}$, aryl and Het (Het$^1$ and Het$^2$) may be substituted, may, when there is a sufficient number of carbon atoms, be linear or branched, and/or be substituted by one or more halo atom."

The terms "Het$^1$alkyl" and "arylalkyl" include Het$^1$C$_{1-6}$ alkyl and arylC$_{1-6}$ alkyl The alkyl groups (e.g. the $C_{1-6}$ alkyl groups) of Het$^1$ alkyl and arylalkyl may, when there is a sufficient number of carbon atoms, be linear or branched, be saturated or unsaturated, and/or be interrupted by oxygen. When used in this context, the terms "Het$^1$" and "aryl" are as defined hereinbefore.

Halo groups with which $R^1$, $R^2$, $R^3$, $R^{12}$, $R^{13}$, aryl, Het$^1$, Het$^2$ and above-mentioned alkyl groups may be substituted or terminated include fluoro, chloro, bromo and iodo.

The term "pharmaceutically, and veterinarily, acceptable derivative" includes salts and solvates. Salts which may be mentioned include: acid addition salts, for example, salts formed with inorganic acids such as hydrochloric, hydrobromic, sulphuric and phosphoric acid, with carboxylic acids or with organo-sulphonic acids; base addition salts; metal salts formed with bases, for example, the sodium and potassium salts. Pharmaceutically acceptable derivatives also include $C_1$ to $C_4$ alkyl ammonium salts.

Preferred compounds of the invention include those wherein $R^{12}$ and $R^{13}$, together with the nitrogen to which they are attached, do not represent an optionally substituted piperazin-4-yl group.

Preferred compounds of the invention include those wherein:

$R^1$ represents Het$^1$C$_{1-6}$alkyl, in which Het$^1$ represents a six-membered aromatic heterocyclic group containing one or more nitrogens;

$R^2$ represents linear, branched, cyclic, or acyclic lower alkyl;

$R^3$ represents linear, branched, cyclic, or acyclic lower alkyl, which is optionally substituted or terminated by $OR^5$ (in which $R^5$ is H or linear, branched, or cyclic $C_1$–$C_3$ alkyl);

$R^{12}$ and $R^{13}$ independently represent H; linear, branched cyclic or acyclic lower (e.g. $C_{1-5}$) alkyl, which alkyl group is optionally substituted and/or terminated by one or more substituents selected from $OR^5$ (in which $R^5$ is H or linear, branched, or cyclic $C_1$–$C_3$ alkyl), Het$^1$ (where Het$^1$ represents a six-membered aromatic heterocyclic group containing one or more nitrogens), or $NR^{10}R^{11}$; Het$^1$ (where Het$^1$ represents a six-membered heterocyclic group containing one or two nitrogens); or, together with the nitrogen atom to which they are attached, represent morpholinyl, tetrahydrothiazinyl, aza- or diazacyclo-$(C_3$–$C_8)$-alkyl (which latter groups are all optionally substituted by one or more substituents selected from oxo, ethyleneketal, $OR^5$ (in which $R^5$ is H or linear, branched, or cyclic $C_1$–$C_3$ alkyl), $NR^{10}R^{11}$ or lower (e.g. $C_{1-4}$) alkyl), or a structural fragment of formula IIa as hereinbefore defined, in which $R^{14}$ and $R^{15}$ independently represent H, linear, branched, cyclic, or acyclic $C_1$–$C_3$ alkyl or $C(O)OR^7$, where $R^7$ represents linear or branched $C_1$–$C_4$ alkyl.

More preferred compounds of the invention include those wherein:

$R^1$ represents pyridinylC$_1$–C$_3$alkyl;

$R^2$ represents linear or branched $C_1$–$C_4$ alkyl;

$R^3$ represents linear or branched $C_1$–$C_3$ alkyl, optionally terminated by $C_{1-2}$ alkoxy;

$R^{12}$ and $R^{13}$ independently represent H (provided that they do not both represent H); linear or branched $C_1$–$C_3$ alkyl, which alkyl group is optionally terminated by one or more substituents selected from $C_{1-2}$ alkoxy, pyridinyl, or $NR^{10}R^{11}$ (in which $R^{10}$ and $R^{11}$ independently represent H or $C_1-C_3$ alkyl); piperidinyl (optionally substituted in the 1(N) position by $COOR^7$ (in which $R^7$ represents linear or branched $C_1-C_4$ alkyl)); pyrazinyl; or, together with the nitrogen atom to which they are attached, represent morpholinyl, tetrahydro-1,4-thiazinyl, azetidinyl, piperidinyl, 1,4-diazacycloheptyl (all of which are optionally substituted by one or more groups selected from linear or branched $C_1-C_3$ alkyl, oxo, ethyleneketal, OH, $C_{1-2}$ alkoxy or $NR^{10}R^{11}$ (where $R^{10}$ and $R^{11}$ independently represent H, straight or branched $C_1-C_3$ alkyl)), or a structural fragment of formula IIb or IIc:

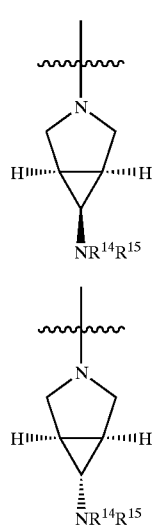

IIb

IIc in which $R^{14}$ and $R^{15}$ either both represent H, or one represents H and the other represents linear, or branched $C_1-C_3$ alkyl or $C(O)OR^7$, where $R^7$ represents linear or branched $C_1-C_4$ alkyl.

Particularly preferred compounds of the invention include those wherein:

$R^1$ represents pyridin-2-yl$C_{1-2}$alkyl (e.g. pyridin-2-ylmethyl);

$R^2$ represents linear $C_{2-3}$ alkyl (e.g. ethyl or n-propyl);

$R^3$ represents $C_2-C_3$ alkyl, optionally terminated by $OCH_3$;

$R^{12}$ and $R^{13}$ independently represent H (provided that they do not both represent H); methyl or ethyl (both of which are optionally terminated with $OCH_3$, $NH_2$, NH(ethyl), N(methyl)$_2$ or pyridin-2-yl); 1-ethyloxycarbonylpiperidinyl; pyrazin-2-yl; or, together with the nitrogen to which they are attached, represent morpholinyl, 4-piperidinyl (optionally substituted by $C_{1-2}$ alkyl, ethyleneketal, oxo and $C_{1-2}$ alkoxy), 1,4-diazacycloheptyl (optionally substituted by $C_{1-2}$ alkyl), azetidinyl (optionally substituted by OH, N(methyl)$_2$ or NH(ethyl)), tetrahydro-1,4-thiazinyl (optionally substituted by dioxo (at the 1,1-position)), or a fragment of formula IId, IIe or IIf:

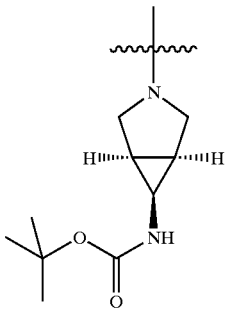

IId

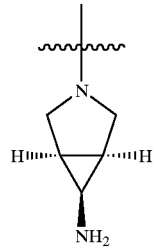

IIe

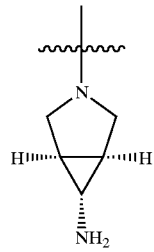

IIf

Most preferred compounds of the invention include the compounds of Examples 1 to 25 described hereinafter.

The compounds of the invention may exhibit tautomerism. All tautomeric forms of the compounds of formulae IA and IB, and mixtures thereof, are included within the scope of the invention.

The compounds of the invention may also contain one or more asymmetric carbon atoms and may therefore,.exhibit optical and/or diastereoisomerism. Diastereoisomers may be separated using conventional techniques e.g. by fractional crystallisation or chromatography. The various stereoisomers may be isolated by separation of a racemic or other mixture of the compounds using conventional techniques e.g. fractional crystallisation or HPLC. The desired optical isomers may be prepared by reaction of the appropriate optically active starting materials under conditions which will not cause racemisation or epimerisation. Alternatively, the desired optical isomers may be prepared by resolution, either by HPLC of the racemate using a suitable chiral support or, where appropriate, by fractional crystallisation of the diastereoisomeric salts formed by reaction of the racemate with a suitable optically active acid or base. All stereoisomers are included within the scope of the invention.

Also included within the scope of the invention are radiolabelled derivatives of compounds of formulae IA and IB which are suitable for biological studies.

PREPARATION

According to a further aspect of the invention there is provided processes for the preparation of compounds of the invention, as illustrated below.

The following processes are illustrative of the general synthetic procedures which may be adopted in order to obtain the compounds of the invention:

1. Compounds of formulae IA and IB may be prepared by reaction of corresponding compounds of formulae IIIA and IIIB, respectively:

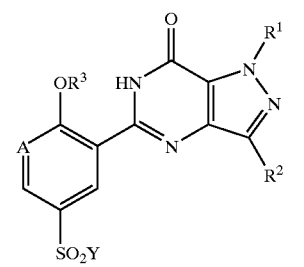

IIIA

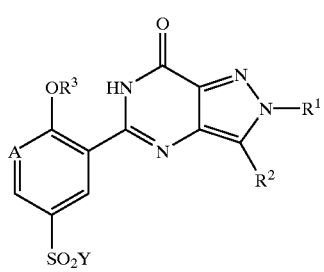

IIIB wherein Y is a leaving group, such as halo, preferably chloro, bromo or iodo, and $R^1$, $R^2$, $R^3$ and A are as previously defined for compounds of formulae IA and IB, with a compound of formula IV:

$$R^{12}R^{13}NH \quad \text{IV}$$

wherein $R^{12}$ and $R^{13}$ are as previously defined for compounds of formulae IA and IB.

This reaction may be performed at or around room temperature, preferably in the presence of an appropriate solvent, such as a $C_1$ to $C_6$ alcohol, acetone/water, or dichloromethane, using an excess of the compound of formula IV and, optionally, in the presence of another suitable base, such as triethylamine. Alternatively, the reaction may be performed at room temperature, in a suitable solvent, such as tetrahydrofuran, using an excess of the anion of the compound of formula IV, formed by reaction of a compound of formula IV with a suitable base (e.g. sodium hydride), in a suitable solvent (e.g. tetrahydrofuran), at or around room temperature.

Compounds of formula IIIA and IIIB, in which A represents N, may be prepared from corresponding compounds of formulae VA and VB, respectively:

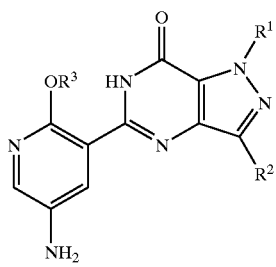

VA

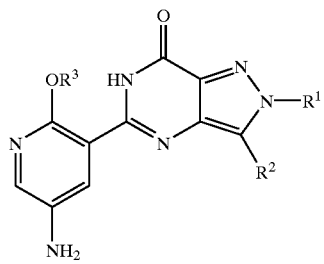

VB wherein $R^1$, $R^2$ and $R^3$ are as previously defined for compounds of formulae IIIA and IIIB, using methods known to those skilled in the art for converting an amino group to an $SO_2Y$ group (in which Y is as previously defined for compounds of formulae IIIA and IIIB). For example, compounds of formulae IIIA and IIIB in which Y is chloro may be prepared by reacting a corresponding compound of formula VA or VB with about a two-fold excess of sodium nitrite in a mixture of concentrated hydrochloric acid and glacial acetic acid, at from about −25° C. to about 0° C., followed by treatment with excess liquid sulphur dioxide and a solution of about a three-fold excess of cupric chloride in aqueous acetic acid, at from about −15° C. to about room temperature.

Compounds of formulae VA and VB may be prepared by cyclisation of corresponding compounds of formulae VIA and VIB, respectively:

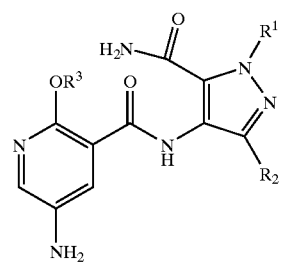

VIA

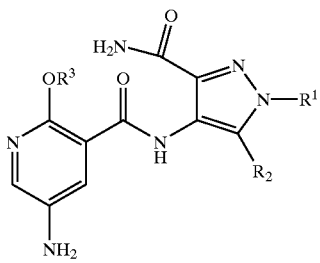

VIB wherein $R^1$, $R^2$ and $R^3$ are as previously defined for compounds of formulae VA and VB.

This cyclisation may be accomplished under basic, neutral or acidic conditions using known methods for pyrimidone ring formation. Preferably, the cyclisation is performed under basic conditions using an alkali metal salt of an alcohol or amine, such as potassium tert-butoxide or potassium bis(trimethylsilyl) amide, in the presence of a suitable solvent (e.g. an alcohol), optionally in the presence of molecular sieves, for example at elevated (e.g. reflux) temperature (or, if performed in a sealed vessel, at above reflux temperature). The skilled person will appreciate that, when an alcohol is selected as solvent, an appropriate alcohol of formula $R^3OH$, or a sterically hindered alcohol, e.g.

3-methyl pentan-3-ol, may be used if it is intended to mitigate alkoxide exchange at the 2-position of the pyridin-3-yl substituent.

Compounds of formulae VIA and VIB may be prepared by the reduction of corresponding compounds of formulae VIIA and VIIB, respectively:

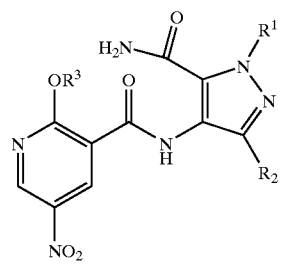

VIIA

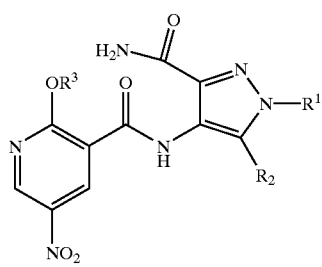

VIIB wherein $R^1$, $R^2$ and $R^3$ are as defined previously for compounds of formulae VIA and VIB, by conventional techniques, such as catalytic hydrogenation or reduction in the presence of $SnCl_2$. Hydrogenation may be achieved using a Raney nickel catalyst in a suitable solvent such as ethanol at a hydrogen pressure of about 150 kPa to 500 kPa, especially 345 kPa, at from about 40° C. to about 50° C.

Compounds of formulae VIIA and VIIB may be prepared by reaction of corresponding compounds of formulae VIIIA and VIIIB, respectively:

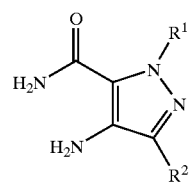

VIIIA

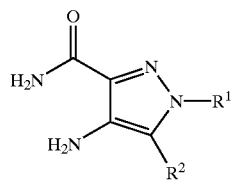

VIIIB wherein $R^1$ and $R^2$ are as defined previously for compounds of formulae VIIA and VIIB, with a compound of formula IX or a carboxylic acid derivative thereof:

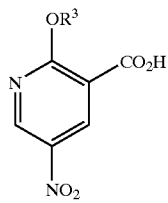

IX wherein $R^3$ is as previously defined for compounds of formulae VIIA and VIIB.

This reaction may be achieved by conventional amide bond forming techniques which are well known to those skilled in the art. For example, an acyl halide (e.g. chloride) derivative of a compound of formula IX may be reacted with a compound of formula VIIIA or VIIIB in the presence of an excess of a tertiary amine, such as triethylamine or pyridine, optionally in the presence of a suitable catalyst, such as 4-dimethylaminopyridine, in a suitable solvent such as dichloromethane, at a temperature of about 0° C. to room temperature.

A variety of other amino acid coupling methodologies may be used to couple the compound of formula VIIIA or VIIIB with the compound of formula IX. For example, the acid of formula IX or a suitable salt thereof (e.g. sodium salt) may be activated with an appropriate activating reagent, e.g. a carbodiimide, such as 1,3-dicyclohexylcarbodiimide or 1-(3-dimethylaminopropyl)-3-ethylcarbodiimide hydrochloride, optionally in the presence of 1-hydroxybenzotriazole hydrate and/or a catalyst such as 4-diaminomethylpyridine; a halotrisaminophosphonium salt such as bromotris(pyrrolidinyl)phosphonium hexafluorophosphate; or a suitable pyridinium salt such as 2-chloro-1-methyl pyridinium chloride. Either type of coupling reaction may be conducted in a suitable solvent such as dichloromethane or tetrahydrofuran, optionally in the presence of a tertiary amine such as N-methylmorpholine or N-ethyldiisopropylamine (for example when either the compound of formula VIIIA or VIIIB, or the activating agent is presented in the form of an acid addition salt), at from about 0° C. to about room temperature.

Alternatively, the carboxylic acid function of compounds of formula IX may be activated using an excess of a reagent such as N,N'-carbonyldiimidazole in an appropriate solvent, e.g. ethyl acetate, dichloromethane or butan-2-one, at from about room temperature to about 80° C., followed by reaction of the intermediate imidazolide with a compound of formula VIIIA or VIIIB at from about 20° C. to about 90° C.

Compounds of formulae IIIA and IIIB, in which A is CH, may be prepared from corresponding compounds of formulae XA and XB, respectively:

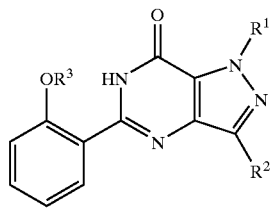

XA

XB

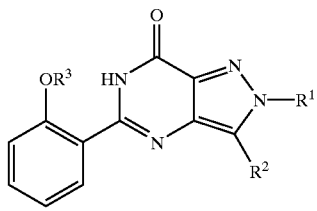

wherein $R^1$, $R^2$ and $R^3$ are as previously defined for compounds of formulae IIIA and IIIB, for example using conventional methods for the introduction of a $SO_2Y$ group into an aromatic ring system, such as reaction of a compound of formula XA and XB with a compound of formula $SO_2Y$ and/or a compound of formula $YSO_3H$. When Y is chloro, an excess of chlorosulphonic acid, optionally with an excess of thionyl chloride, at from about 0° C. to room temperature may be used in an appropriate organic solvent (e.g. dichloromethane).

Compounds of formulae XA and XB in which $R^1$ represents alkylHet¹ or alkylaryl may be prepared by alkylation of corresponding compounds of formulae XIA and XIB, respectively:

XIA

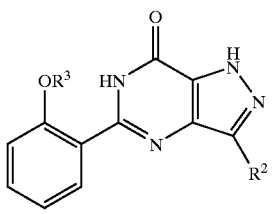

XIB

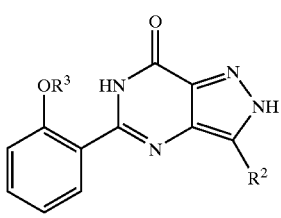

wherein $R^2$ and $R^3$ are as previously defined for compounds of formulae XA and XB, using methods which are well known to those skilled in the art. For example, this reaction may be accomplished by reaction of a compound of formula XIA or XIB with a compound of formula $R^{1a}L^1$, wherein $R^{1a}$ represents alkylHet¹ or alkylaryl, and $L^1$ is a suitable leaving group, using conventional techniques which are well known to those skilled in the art. Preferably, the leaving group is halo (preferably chloro, bromo or iodo) and the alkylation is performed in the presence of an appropriate base (e.g. sodium hydride or potassium bis(trimethylsilyl) amide), in an appropriate solvent (e.g. dimethylformamide, toluene, or tetrahydrofuran), optionally in the presence of sodium iodide or potassium iodide, at from about room temperature to about 50° C. Preferably the alkylation is conducted at between about 40° C. to about 50° C. Alternatively, compounds of formulae XVA and XVB may be reacted with a compound of formula $R^{1a}OH$, wherein $R^{1a}$ represents alkylHet, or alkylaryl, using classical Mitsunobu methodology.

Compounds of formulae XIA and XIB may be prepared by cyclisation of corresponding compounds of formulae XIIA and XIIB, respectively:

XIIA

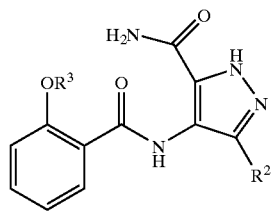

XIIB

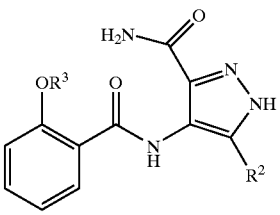

wherein $R^2$ and $R^3$ are as previously defined for compounds of formulae XIA and XIB. This cyclisation may be accomplished using analogous conditions to those described previously for preparation of compounds of formulae VA and VB.

Compounds of formulae XIIA and XIIB may be prepared by coupling corresponding compounds of formulae XIIIA and XIIIB, respectively:

XIIIA

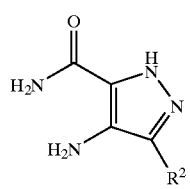

XIIIB

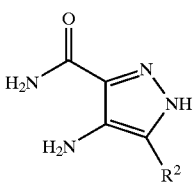

wherein $R^2$ is as previously defined for compounds of formulae XIIA and XIIB, with a compound of formula XIV or a carboxylic acid derivative thereof:

XIV

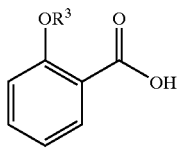

wherein $R^3$ is as previously defined for compounds of formulae XIIA and XIIB, using techniques known to those skilled in the art. For example, the reaction may be achieved using analogous amide bond forming techniques to those previously described for preparation of compounds of formulae VIIA and VIB.

Alternatively, compounds of formulae XA and XB, as defined hereinbefore, may alternatively be prepared by cyclisation of corresponding compounds of formulae XVA and XVB, respectively:

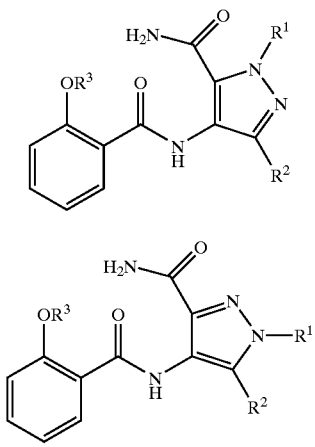

XVA

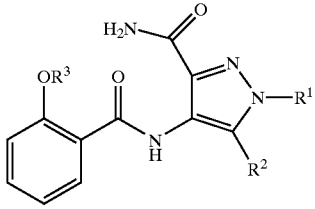

XVB wherein $R^1$, $R^2$ and $R^3$ are as previously defined for compounds of formulae XA and XB. This cyclisation may be accomplished using analogous conditions to those described previously for preparation of compounds of formulae VA and VB.

Compounds of formulae XVA and XVB may be prepared by reacting corresponding compounds of formulae VIIIA and VIIIB, as defined hereinbefore, with a compound of formula XIV, as defined hereinbefore, or a carboxylic acid derivative thereof. The reaction may be achieved using analogous amide bond forming techniques to those previously described for preparation of compounds of formulae VIIA and VIIB.

Compounds of formulae VIIIA and VIIIB are available using known techniques. For example, compounds of formulae VIIIA and VIIIB in which $R^1$ represents alkylHet$^1$ or alkylaryl, may be prepared by alkylation of corresponding compounds of formulae XIIIA and XIIIB, for example using analogous methods to those described hereinbefore. For example, compounds of formulae XIIIA and XIIIB may be reacted with a compound of formula $R^{1a}L^1$ as hereinbefore defined, using conventional techniques. Preferably, the leaving group is halo (preferably chloro, bromo or iodo) and the alkylation is performed in the presence of an appropriate base (e.g. cesium carbonate), in an appropriate solvent (e.g. dimethyl formamide, or acetonitrile), optionally in the presence of sodium iodide or potassium iodide, at from about room temperature to about 80° C.

2. Compounds of formulae IA and IB may be prepared by cyclisation of corresponding compounds of formulae XVIA and XVIB, respectively:

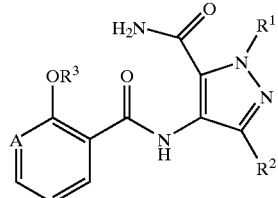

XVIA

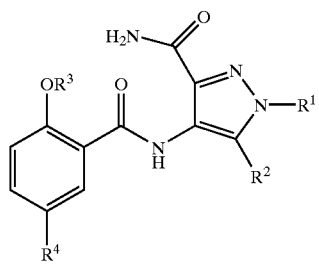

XVIB wherein $R^1$, $R^2$, $R^3$, $R^4$ and A are as defined previously for compounds of formulae IA and IB. This cyclisation may be achieved using analogous pyrimidone ring formation techniques to those described previously for the preparation of compounds of formulae VA and VB.

Compounds of formulae XVIA and XVIB may be prepared by reaction of corresponding compounds of formulae VIIIA and VIIIB, as defined hereinbefore, with a compound of formula XVII, or an acid derivative thereof:

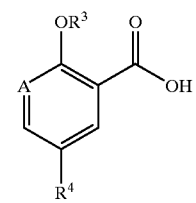

XVII wherein $R^3$, $R^4$ and A are as previously defined for compounds of formulae XVIA and XVIB. This reaction may be achieved using analogous amide bond forming techniques to those previously described for the preparation of compounds of formulae VIIA and VIIB.

3. Compounds of formulae IA and IB in which $R^1$ represents alkylHet or alkylaryl may be prepared by alkylation of corresponding compounds of formulae XVIIIA and XVIIIB, respectively:

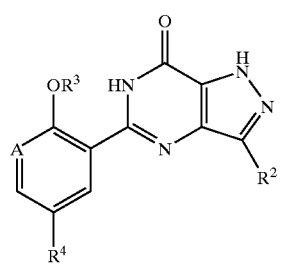

XVIIIA

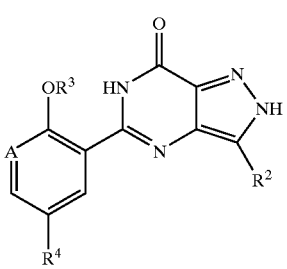

XVIIIB wherein $R^2$, $R^3$, $R^4$ and A are as previously defined for compounds of formulae IA and IB, for example using analogous techniques to those described hereinbefore for preparation of compounds of formulae XA and XB. Compounds of formulae XVIIIA and XVIIIB may be prepared by analogy with methods described herein.

Compounds of formulae IV, IX, XIIIA and XIIIB, XIV, XVII, and compounds of formulae $HNR^{12}R^{13}$ (in which $R^{12}$ and $R^{13}$ are as defined hereinbefore) and $R^{1a}L^1$ and $R^{1a}OH$ (in which $R^{1a}$ and $L^1$ are as defined hereinbefore), and derivatives thereof, when not commercially available or not subsequently described, may be obtained either by analogy with the processes described hereinbefore, or by conventional synthetic procedures, in accordance with standard techniques, from readily available starting materials using appropriate reagents and reaction conditions.

Substituents on aryl and Het ($Het^1$ and $Het^2$) groups in the above-mentioned compounds may be introduced, removed and interconverted, using techniques which are well known to those skilled in the art.

The skilled person will also appreciate that various standard substituent or functional group interconversions and transformations within certain compounds of formulae IA and IB will provide other compounds of formulae IA and IB. For example, alkoxide exchange at the 2-position of the 5-phenyl and the pyridin-3-yl substituents. Moreover, certain compounds of formulae IA and IB, for example those in which $R^{12}$ and $R^{13}$, together with the nitrogen to which they are attached, form a N-alkyl-diazacyclo-($C_3$–$C_{12}$)-alkyl group, may be prepared directly from the corresponding compounds of formulae IA and IB in which $R^{12}$ and $R^{13}$, together with the nitrogen to which they are attached, form a diazacyclo-($C_3$–$C_{12}$)-alkyl group using standard alkylation procedures.

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it is desirable to protect include oxo, hydroxy, amino and carboxylic acid. Suitable protecting groups for oxo include acetals, ketals (e.g. ethylene ketals) and dithianes. Suitable protecting groups for hydroxy include trialkylsilyl and diarylalkylsilyl groups (e.g. tert-butyldimethylsilyl, tert-butyldiphenylsilyl or trimethylsilyl) and tetrahydropyranyl. Suitable protecting groups for amino include tert-butyloxycarbonyl, 9-fluorenylmethoxycarbonyl or benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art.

The use of protecting groups is fully described in "Protective Groups in Organic Chemistry", edited by JWF McOmie, Plenum Press (1973), and "Protective Groups in Organic Synthesis", $2^{nd}$ edition, TW Greene & PGM Wutz, Wiley-Interscience (1991).

Persons skilled in the art will also appreciate that, in order to obtain compounds of formulae IA and IB in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Pharmaceutically acceptable acid addition salts of the compounds of formulae IA and IB which contain a basic centre may be prepared in a conventional manner. For example, a solution of the free base may be treated with the appropriate acid, either neat or in a suitable solvent, and the resulting salt may then be isolated either by filtration of by evaporation under vacuum of the reaction solvent. Pharmaceutically acceptable base addition salts can be obtained in an analogous manner by treating a solution of a compound of formula IA or IB with the appropriate base. Both types of salt may be formed or interconverted using ion-exchange resin techniques.

It will be appreciated by those skilled in the art that certain protected derivatives of compounds of formula I, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula I may act as prodrugs of other compounds of formula I.

All protected derivatives, and prodrugs, of compounds of formula I are included within the scope of the invention.

MEDICAL USE

The compounds of the invention are useful because they possess pharmacological activity in animals, especially mammals, including humans. They are therefore indicated as pharmaceuticals, as well as for use as animal medicaments.

According to a further aspect of the invention there is provided the compounds of the invention for use as pharmaceuticals, and for use as animal medicaments.

In particular, compounds of the invention have been found to be potent and selective inhibitors of cGMP PDEs, such as cGMP PDE5, for example as demonstrated in the tests described below, and are thus useful in the treatment of medical conditions in humans, and in animals, in which cGMP PDEs, such as cGMP PDE5, are indicated, and in which inhibition of cGMP PDEs, such as cGMP PDE5, is desirable.

By the term "treatment", we include both therapeutic (curative) or prophylactic treatment.

Thus, according to a further aspect of the invention there is provided the use of the compounds of the invention in the manufacture of a medicament for the treatment of a medical condition in which a cGMP PDE (e.g. cGMP PDE5) is indicated. There is further provided the use of the compounds of the invention in the manufacture of a medicament for the treatment of a medical condition in which inhibition of a cGMP PDE (e.g. cGMP PDE5) is desirable.

The compounds of the invention are thus expected to be useful for the curative or prophylactic treatment of male erectile dysfunction (MED), female sexual dysfunction (FSD), premature labour, dysmenorrhoea, benign prostatic hyperplasia (BPH), bladder outlet obstruction, incontinence, stable and unstable variant (Prinzmetal) angina, hypertension, pulmonary hypertension, congestive heart failure, atherosclerosis, stroke, peripheral vascular disease, conditions of reduced blood vessel patency (e.g. post transluminal coronary angioplasty (post-PTCA)), chronic asthma, bronchitiS, allergic asthma, allergic rhinitis, glaucoma or diseases characterised by disorders of gut motility (e.g. irritable bowel syndrome (IBS)). Other conditions which may be mentioned include pre-eclampsia, Kawasaki's syndrome, nitrate tolerance, multiple sclerosis, peripheral diabetic neuropathy, stroke, Alzheimer's disease, acute respiratory failure, psoriasis, skin necrosis, cancer metastasis, baldness, nutcracker oesophagus, anal fissure and hypoxic vasoconstriction. Particularly preferred conditions include MED and FSD.

Thus, the invention provides a method of treating or preventing a medical condition for which a cGMP PDE5 inhibitor is indicated, in an animal (e.g. a mammal, including a human being), which comprises administering a therapeutically effective amount of a compound of the invention to a mammal in need of such treatment.

PHARMACEUTICAL PREPARATIONS

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The compounds of the invention may also be combined with any other drugs useful in the inhibition of cGMP PDEs, such as cGMP PDE5.

In human therapy, the compounds of the invention can be administered alone but will generally be administered in admixture with a suitable pharmaceutical excipient diluent or carrier selected with regard to the intended route of administration and standard pharmaceutical practice.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the invention will usually be from 10 to 500 mg/kg (in single or divided doses).

Thus, for example, the tablets or capsules of the compound of the invention may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™ or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg, which may be administered in a single dose or, more usually, in divided doses throughout the day.

Alternatively, the compounds of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route, particularly for treating diseases of the eye.

For ophthalmic use, the compounds of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The skilled person will also be appreciated that, in the treatment of certain conditions (including MED and FSD), compounds of the invention may be taken as a single dose on an "as required" basis (i.e. as needed or desired).

Generally, in humans, oral administration of the compounds of the invention is the preferred route, being the most convenient and, for example in MED, in avoiding the well-known disadvantages associated with intracavernosal (i.c.) administration.

A preferred oral dosing regimen in MED for a typical man is from 25 to 250 mg of compound when required.

In circumstances where the recipient suffers from a swallowing disorder or from impairment of drug absorption after oral administration, the drug may be administered parenterally, e.g. sublingually or bucally.

For veterinary use, compounds of the invention may administered as a suitably acceptable formulation in accordance with normal veterinary practice and the veterinary surgeon will determine the dosing regimen and route of administration which will be most appropriate for a particular animal.

Thus, according to a further aspect of the invention there is provided a pharmaceutical formulation including a compound of the invention in admixture with a pharmaceutically or veterinarily acceptable adjuvant, diluent or carrier.

In addition to the fact that compounds of the invention inhibit cyclic guanosine 3',5'-monophosphate phosphodiesterases (cGMP PDEs) and in particular, are potent and selective inhibitors of cGMP PDE5, compounds of the invention may also have the advantage that they may be more efficacious than, be less toxic than, have a broader range of activity than, be more potent than, produce fewer side effects than, be more easily absorbed than, or they may have other useful pharmacological properties over, compounds known in the prior art.

The biological activities of the compounds of the present invention were determined by the following test methods.

BIOLOGICAL TESTS

Phosphodiesterase (PDE) Inhibitory Activity

In vitro PDE inhibitory activities against cyclic guanosine 3',5'-monophosphate (cGMP) and cyclic adenosine 3',5'-monophosphate (cAMP) phosphodiesterases were determined by measurement of their $IC_{50}$ values (the concentration of compound required for 50% inhibition of enzyme activity).

The required PDE enzymes were isolated from a variety of sources, including human corpus cavernosum, human and rabbit platelets, human cardiac ventricle, human skeletal muscle and bovine retina, essentially by the method of W. J. Thompson and M. M. Appleman (Biochem., 1971, 10, 311). In particular, the cGMP-specific PDE (PDE5) and the cGMP-inhibited cAMP PDE (PDE3) were obtained from human corpus cavernosum tissue, human platelets or rabbit platelets; the cGMP-stimulated PDE (PDE2) was obtained from human corpus cavernosum; the calcium/calmodulin (Ca/CAM)-dependent PDE (PDE1) from human cardiac ventricle; the cAMP-specific PDE (PDE4) from human skeletal muscle; and the photoreceptor PDE (PDE6) from bovine retina.

Assays were performed using modification of the "batch" method of W. J. Thompson et al. (Biochem., 1979, 18, 5228). Results from these tests show that the compounds of the present invention are potent and selective inhibitors of cGMP-specific PDE5.

Functional Activity

This was assessed in vitro by determining the capacity of a compound of the invention to enhance sodium nitroprusside-induced relaxation of precontracted rabbit corpus cavernosum tissue strips, as described by S. A. Ballard et al. (Brit. J. Pharmacol., 1996, 118 (suppl.), abstract 153P).

In Vivo Activity

Compounds may be screened in anaesthetised dogs to determine their capacity, after i.v. administration, to enhance the pressure rises in the corpora cavernosa of the penis induced by intracavernosal injection of sodium nitroprusside, using a method based on that described by Trigo-Rocha et al. (Neurourol. and Urodyn., 1994, 13, 71).

Safety Profile

Compounds of the invention may be tested at varying i.v and p.o. doses in animals such as mouse and dog, observing for any untoward effects.

EXAMPLES AND PREPARATIONS

The synthesis of the compounds of the invention and of the intermediates for use therein are illustrated by the following Examples and Preparations.

$^1$H nuclear magnetic resonance (NMR) spectra were recorded using either a Varian Unity 300 or a Varian Inova 400 spectrometer and were in all cases consistent with the proposed structures. Characteristic chemical shifts ($\delta$) are given in parts-per-million downfield from tetramethylsilane using conventional abbreviations for designation of major peaks: eg s, singlet; d, doublet; t, triplet; q, quartet; m, multiplet; br, broad.

Mass spectra (m/z) were recorded using a Fisons Instruments Trio mass spectrometer in the thermospray ionisation mode. Room temperature includes 20 to 25° C.

Synthesis of Intermediates

Preparation 1

Ethyl 3-ethyl-1H-pyrazole-5-carboxylate

Ethanolic sodium ethoxide solution (21% w/w; 143 ml, 0.39 mol) was added dropwise to a stirred, ice-cooled solution of diethyl oxalate (59.8 ml, 0.44 mol) in absolute ethanol (200 ml) under an atmosphere of nitrogen and stirred for 15 minutes. Butan-2-one (39 ml, 0.44 mol) was added dropwise and the reaction mixture stirred for 18 hours warming to room temperature and then for 6 hours at 40° C. The resultant mixture was cooled to 0° C., glacial acetic acid (25 ml, 0.44 mol) was added dropwise and stirred for 30 minutes at 0° C. Hydrazine hydrate (20 ml, 0.44 mol) was added dropwise and the reaction mixture was allowed to warm to room temperature and stirred for 18 hours. The solvent was removed under reduced pressure and ,the residue was partitioned between dichloromethane (300 ml) and water (100 ml). The organic layer was separated and washed with water (2×100 ml), dried over $Na_2SO_4$ and concentrated under reduced pressure to give the title compound (66.0 g).

$\delta(CDCl_3)$: 1.04 (3H,t), 1.16 (3H,t), 2.70 (2H,q), 4.36 (2H,q), 6.60 (1H,s).

LRMS: m/z 169 (M+1)$^+$.

Preparation 2

3-Ethyl-1H-pyrazole-5-carboxylic acid

Aqueous sodium hydroxide solution (10M; 100 ml) was added dropwise to a stirred suspension of the title compound of preparation 1 (66.0 g, 0.39 mol) in methanol and heated under reflux for 4 hours. The reaction mixture was cooled and the solvent removed under reduced pressure to ca. 200 ml, diluted with water (200 ml) and washed with toluene (3×100 ml). The resulting aqueous layer was acidified to pH 4 with concentrated hydrochloric acid and the white precipitate filtered and dried by suction to afford the tide compound as a white solid (34.1 g).

$\delta(d_6\text{-DMSO})$: 1.13 (3H,t), 2.56 (2H,q), 6.42 (1H,s).

Preparation 3

4-Nitro-3-n-propyl-1H-pyrazole-5-carboxylic acid

Fuming sulfuric acid (17.8 ml) was added dropwise to stirred, ice-cooled fuming nitric acid (16.0 ml). The resulting solution was heated to 50° C. and 3-n-propyl-1H-pyrazole-5-carboxylic acid (16.4 g, 0.106 mol; Chem. Pharm. Bull., 1984, 32, 1568) added portionwise over 30 minutes whilst maintaining the reaction temperature below 60° C. The resulting solution was heated for 18 hours at 60° C., allowed to cool, then poured onto ice. The white precipitate was filtered, washed with water and dried by suction to yield the title compound as a white solid (15.4 g), m.p. 170–172° C.

$\delta(d_6\text{-DMSO})$: 0.90 (3H,t), 1.64 (2H,m), 2.83 (2H,m), 14.00 (1H,s).

Found: C, 42.35; H, 4.56; N, 21.07. $C_7H_9N_3O_4$ requires C, 42.21; H, 4.55; N, 21.10%.

Preparation 4

3-Ethyl-4-nitro-1H-pyrazole-5-carboxylic acid

Obtained from the title compound of preparation 2, using an analogous method to preparation 3, as a brown solid (64%).

$\delta(d_6\text{-DMSO})$: 1.18 (3H,t), 2.84 (2H,m), 13.72 (1H,s).

Preparation 5

4-Nitro-3-n-propyl-1H-pyrazole-5-carboxamide

A solution of the title compound of preparation 3 (15.4 g, 0.08 mol) in thionyl chloride (75 ml) was heated under reflux for 3 hours. The reaction mixture was cooled and the solvent removed under reduced pressure. The residue was azeotroped with tetrahydrofuran (2×50 ml), then suspended in tetrahydrofuran (50 ml), stirred at 0° C. and treated with gaseous ammonia for 1 hour. Water (50 ml) was added and the resulting mixture concentrated under reduced pressure to give a solid. The solid was triturated with water, filtered and dried under suction to afford the title compound as a white solid (14.3 g), m.p. 197–199° C.

$\delta(d_6\text{-DMSO})$: 0.90 (3H,t), 1.68 (2H,m), 2.86 (2H,t), 7.68 (1H,s), 8.00 (1H,s).

Found: C, 42.35; H, 5.07; N, 28.38. $C_7H_{10}N_4O_3$ requires C, 42.42; H, 5.09; N, 28.27%.

Preparation 6

3-Ethyl-4-nitro-1H-pyrazole-5-carboxamide

Obtained from the title compound of preparation 4, using an analogous method to preparation 5, as a white solid (90%).

$\delta(d_6\text{-DMSO})$: 1.17 (3H,t), 2.87 (2H,m), 7.40 (1H,s), 7.60 (1H,s), 7.90 (1H,s).

LRMS: m/z 185 (M+1)$^+$.

Preparation 7

4-Amino-3-n-propyl-1H-pyrazole-5-carboxamide

A stirred mixture of the title compound of preparation 5 (10.0 g, 0.05 mol), 10% palladium on charcoal (1.5 g) and ethanol (400 ml) was hydrogenated for 18 hours at 50 psi and 50° C., then filtered. The filter pad was washed with ethanol (200 ml) and the combined filtrate evaporated under reduced pressure to give an orange solid which was recrystallised from ethyl acetate:methanol to afford the title compound as a white solid (6.8 g). m.p. 196–201° C.

$\delta(d_6\text{-DMSO})$: 0.88 (3H,t), 1.55 (2H,m), 2.46 (2H,t), 4.40 (2H,s), 7.00 (1H,s), 7.12 (1H,s), 12.20 (1H,s).

Found: C, 48.96; H, 6.98; N, 32.08. $C_7H_{12}N_4O$; 0.25 $H_2O$ requires C, 48.68; H, 7.30; N, 32.44%.

Preparation 8

4-Amino-3-ethyl-1H-pyrazole-5-carboxamide

Obtained from the title compound of preparation 6, using an analogous method to preparation 7, as a brown solid (80%).

$\delta(d_6\text{-DMSO})$: 1.08 (3H,t), 2.45 (2H,q), 4.50 (1H,s), 6.88 (1H,s), 7.10 (1H,s), 7.26 (2H,s).

LRMS: m/z 155 (M+1)$^+$.

Preparation 9

4-(2-n-Propoxybenzamido)-3-n-propyl-1H-pyrazole-5-carboxamide

A solution of 2-n-propoxybenzoyl chloride (57.6 g, 0.29 mol) in dichloromethane (50 ml) was added dropwise to a solution of the title compound of preparation 7 (35.0 g, 0.21 mol) in dry pyridine (350 ml) at 0° C. and stirred for 18 hours at room temperature. The solvent was removed under reduced pressure and the residue was azeotroped with toluene (2×100 ml). The resulting brown solid was triturated with diethyl ether (100 ml) to give the title compound (83.0 g) as a beige solid.

$\delta(CD_3OD)$: 0.92 (3H,t), 1.14 (3H,t), 1.65 (2H,m), 1.94 (2H,m), 2.80 (2H,t), 4.20 (2H,t), 7.08 (1H,m), 7.18 (1H,d), 7.52 (1H,m), 8.04 (1H,d).

LRMS: m/z 331 (M+1)$^+$.

Preparation 10

3-Ethyl-4-(2-n-propoxybenzamido)-1H-pyrazole-5-carboxamide

Obtained from the title compound of preparation 8 and 2-n-propoxybenzoyl chloride, using an analogous method to preparation 9, as a beige solid (68%).

δ(d$_6$-DMSO): 0.93 (3H,t), 1.12 (3H,t), 1.86 (2H,q), 2.71 (2H,m), 4.15 (2H,t), 7.06 (1H,m), 7.20 (1H,d), 7.20 (1H,s), 7.40 (1H,s), 7.50 (1H,m), 7.92 (1H,d), 10.20 (1H,s).

LRMS: m/z 317 (M+1)$^+$.

Preparation 11

4-(2-Ethoxybenzamido)-3-n-propyl-1H-pyrazole-5-carboxamide

Obtained from the title compound of preparation 7 and 2-ethoxybenzoyl chloride, using an analogous method to preparation 9, as a white solid (64%), m.p. 209–211° C.

δ(d$_6$-DMSO): 0.82 (3H,t), 1.42 (3H,t), 1.56 (2H,m), 1.75 (2H,t), 4.27 (2H,q), 7.07 (1H,m), 7.22 (2H,m), 7.52 (2H,m), 8.00 (1H,d), 10.40 (1H,s), 12.96 (1H,s).

Found: C, 60.73; H, 6.41; N, 17.80. $C_{16}H_{20}N_4O_3$ requires C, 60.74; H, 6.37; N, 17.71%.

Preparation 12

5-(2-n-Propoxyphenyl)-3-n-propyl-1,6-dihydro-7H-pyrazolo[4,3-d]pyrimidin-7-one

Potassium tert-butoxide (93.0 g, 0.83 mol) was added portionwise to a stirred solution of the title compound of preparation 9 (83.0 g, 0.25 mol) in propan-2-ol (800 ml) under an atmosphere of nitrogen and heated for 18 hours under reflux. The reaction mixture was cooled and water (100 ml) was added, to produce a homogeneous solution which was acidified to pH 6 with hydrochloric acid (2M). The resulting white precipitate was filtered and dried by suction to afford the title compound as a white solid (37.4 g).

δ(CDCl$_3$): 1.05 (3H,t), 1.16 (3H,t), 2.00 (4H,m), 3.04 (2H,t), 4.20 (2H,t), 7.07 (1H,d), 7.16 (1H,m), 7.48 (1H,m), 8.52 (1H,d), 11.30 (1H,s), 12.25 (1H,s).

LRMS: m/z 313 (M+1)$^+$.

Found: C, 65.36; H, 6.49; N, 17.99. $C_{17}H_{20}N_4O_2$ requires C, 65.37; H, 6.45; N, 17.94%.

Preparation 13

3-Ethyl-5-(2-n-propoxyphenyl)-1,6-dihydro-7H-pyrazolo[4,3-d]pyrimidin-7-one

Obtained from the title compound of preparation 10, using an analogous method to preparation 12, as a white solid (85%).

δ(d$_6$-DMSO): 0.95 (3H,t), 1.15 (3H,t), 1.72 (2H,m), 2.84 (2H,q), 4.03 (2H,t), 7.06 (1H,m), 7.15 (1H,d), 7.44 (1H,m), 7.72 (1H,d), 11.83 (1H,s), 13.64 (1H,s).

LRMS: m/z 299 (M+1)$^+$.

Preparation 14

5-(2-Ethoxyphenyl)-3-n-propyl-1,6-dihydro-7H-pyrazolo[4,3-d]pyrimidin-7-one

Obtained from the title compound of preparation 11, using an analogous method to preparation 12, as a white solid (88%), m.p. 199–201° C.

δ(CDCl$_3$): 1.08 (3H,t), 1.65 (3H,t), 1.98 (2H,m), 3.04 (2H,t), 4.36 (2H,q), 7.10 (1H,d), 7.20 (1H,m), 7.50 (1H,m), 8.57 (1H,d), 11.36 (1H,s), 11.88 (1H,s).

Found: C, 64.44; H, 6.19; N, 18.44. $C_{16}H_{18}N_4O_2$ requires C, 64.41; H, 6.08; N, 18.78%.

Preparation 15

5-(2-n-Propoxyphenyl)-3-n-propyl-2-(pyridin-2-yl)methyl-2,6-dihydro-7H-pyrazolo[4,3-d]pyrimidin-7-one Sodium hydride (60% dispersion in mineral oil; 704 mg, 17.61 mmol) was slowly added to a solution of the title compound of preparation 12 (5.0 g, 16 mmol) in tetrahydrofuran (100 ml), and the mixture stirred at room temperature for 1 hour. 2-(Chloromethyl)pyridine (obtained from 2.45 g, 19.21 mol of the hydrochloride salt) was added to the reaction mixture and then stirred at 50° C. for 18 hours. The mixture was quenched with water (75 ml) and tetrahydrofuran was removed under reduced pressure. The aqueous residue was extracted with ethyl acetate (200 ml), the organic extracts were dried over MgSO$_4$, filtered and concentrated under reduced pressure. The residue was purified by column chromatography on silica gel eluting with a gradient system of hexane:ethyl acetate (65:35 to 50:50) to afford the title compound as a white solid (2.56 g).

δ(CDCl$_3$): 1.00 (3H,t), 1.15 (3H,t), 1.70 (2H,m), 2.00 (2H,m), 3.00 (2H,t), 4.20 (2H,t), 5.75 (2H,s), 7.05–7.15 (1H,m), 7.20 (1H,m), 7.45 (1H,m), 7.65 (1H,m), 8.40 (1H,d), 8.60 (1H,d), 10.90 (1H,s).

LRMS: m/z 404 (M+1)$^+$.

Preparation 16

3-Ethyl-5-(2-n-propoxyphenyl)-2-(pyridin-2-yl)methyl-2,6-dihydro-7H H-pyrazolo[4,3-d]pyrimidin-7-one The title compound of preparation 13 (20 g, 67.3 mmol) was suspended in toluene (450 ml ) and cooled to 0° C. Potassium bis(trimethylsilyl)amide (0.5M in toluene, 135 ml, 67.5 mmol) was added over 10 minutes and reaction mixture was warmed to room temperature and stirred for 1 hour. 2-(Chloromethyl)pyridine (obtained from 8.6 g (67.4 mmol) of the hydrochloride salt) was added and the reaction mixture was stirred at 45° C. for 18 hours. The reaction was quenched with water (200 ml) then partitioned between water (200 ml) and ethyl acetate (1000 ml). The layers were separated and the aqueous layer extracted with ethyl acetate (2×100 ml). The combined organic layers were dried over Na$_2$SO$_4$, filtered and concentrated under reduced pressure. The residue was purified by column chromatography on silica gel eluting with a gradient system of pentane:ethyl acetate:triethylamine (50:50:0.5 to 25:75:0.5) then recrystallised from ethyl acetate to afford the title compound as a white solid (12.8 g).

δ(CDCl$_3$): 1.10 (3H,t), 1.30 (3H,t), 2.00 (2H,m), 3.00 (2H,q), 4.20 (2H,t), 5.70 (2H,s), 7.00–7.15 (3H,m), 7.20 (1H,m), 7.40 (1H,m), 7.60 (1H,m), 8.40 (1H,d), 8.60 (1H,d), 10.90 (1H,s).

LRMS: m/z 390 (M+1)$^+$.

Preparation 17

5-(2-Ethoxyphenyl)-3-n-propyl-2-(pyridin-2-yl)methyl-2,6-dihydro-7H-pyrazolo[4,3-d]pyrimidin-7-one Obtained from the title compound of preparation 14 and 2-(chloromethyl) pyridine using an analogous method to preparation 15, as a white foam (64%).

δ(CDCl$_3$): 1.00 (3H,t), 1.60 (3H,t), 1.75 (2H,m), 3.00 (2H,t), 4.30 (2H,q), 5.70 (2H,s), 7.05 (2H,m), 7.15 (1H,m), 7.20 (1H,m), 7.45 (1H,m), 7.60 (1H,m), 8.40 (1H,d), 8.60 (1H,d), 10.90 (1H,s).

LRMS: m/z 390 (M+1)$^+$.

Preparation 18

3-Ethyl-4-nitro-2-(pyridin-2-yl)methyl-pyrazole-5-carboxamide

Cesium carbonate (1.414 kg, 4.34 mol ) was added to a suspension of the title compound of preparation 6 (800 g, 4.34 mol) in acetonitrile (5 L) and the mixture warmed to 60° C. 2-(Chloromethyl)pyridine (obtained from 664.7 g, 5.23 mol of the hydrochloride salt) was added and the reaction heated at 70° C. for 7 hours. Water (9.5 L) was added and the reaction mixture cooled to 10° C. Granulation of this mixture gave a precipitate which was filtered and dried to afford 3-ethyl-4-nitro-1-(pyridin-2-yl) methyl-pyrazole-5-carboxamide (367 g). Sodium chloride (1.58 kg) was added to the filtrate and the solution extracted with ethyl acetate (4×1.75 L). The organic layers were combined and approximately 10 L of solvent removed under reduced pressure. Toluene (5.6 L) was added over 35 minutes to the hot (69–76° C.) solution and then allowed to cool. The resulting suspension was granulated at <10° C. for 30 minutes, filtered, the solid washed with ethyl acetate:toluene (50:50) (600 ml) and dried (60° C.) to afford the title compound as a light brown solid (624 g).

$\delta(d_6$-DMSO): 1.08 (3H, t), 3.02 (2H, q), 5.53 (2H, s), 7.34 (2H, m), 7.65 (1H, s), 7.82 (1H, m), 7.93 (1H, s), 8.52 (1H, d).

LRMS: m/z 275 (M)$^+$

Preparation 19

4-Nitro-3-n-propyl-2-(pyridin-2-yl)methyl-pyrazole-5-carboxamide 2-(Chloromethyl)pyridine hydrochloride (24.6 g, 150 mmol) was added portionwise to a solution of the title compound of preparation 5 (30.0 g, 150 mmol) and cesium carbonate (123.5 g, 380 mmol) in dimethylformamide (300 ml) and stirred at room temperature for 18 hours. The solvent was removed under reduced pressure, the residue suspended in water, and the resulting solid filtered and dried under suction. The residue was purified by column chromatography on silica gel eluting with a solvent system of dichloromethane:methanol (98:2) and repeated using ethyl acetate: pentane (80:20) to afford the title compound as a white solid (16.7 g).

$\delta(d_6$-DMSO): 0.85 (3H, t), 1.45 (2H,m), 2.95 (2H, t), 5.50 (2H, s), 7.30 (2H, m), 7.60 (1H, s), 7.80 (1H, m), 7.90 (1H, s), 8.50 (1H, d).

Preparation 20

4-Amino-3-ethyl-2-(pyridin-2-yl)methyl-pyrazole-5-carboxamide

A mixture of Lindlar catalyst (2 g) and the tide compound of preparation 18 (20 g, 72.7 mmol) in ethanol (160 ml) was hydrogenated for 48 hours at 345 kPa (50 psi) and 50° C., then cooled and filtered. The filtrate was combined with an IMS wash (50 ml) of the filter pad and concentrated under reduced pressure to a volume of 100 ml. The remaining ethanol was removed by distillation, and replaced with ethyl acetate until a head temperature of 77° C. had been achieved. The cooled mixture was granulated at 4° C., filtered and dried to afford the title compound as a light brown solid (13.17 g, 73%).

$\delta(d_6$-DMSO): 0.90 (3H, t), 2.55 (2H, q), 4.50 (2H, s), 5.30 (2H, s), 6.90 (1H, d), 6.95 (1H, s), 7.10 (1H, s), 7.30 (1H, m), 7.75 (1H, m), 8.50 (1H, d).

LRMS: m/z 246 (M+1)$^+$

Preparation 21

4-Amino-3-n-propyl-2-(pyridin-2-yl)methyl-pyrazole-5-carboxamide

A mixture of the title compound of preparation 19 (1.0 g, 3.46 mmol) and Raney nickel (1 g) in ethanol (50 ml) was hydrogenated for 18 hours at 345 kPa (50 psi) and 50° C., then cooled and filtered. The filtrate was combined with an ethanol (50 ml) wash of the filter pad and the solvent removed under reduced pressure, to afford the title compound as a crystalline solid (830 mg).

$\delta(d_6$-DMSO): 0.80 (3H, t), 1.35 (2H, m), 3.30 (2H, t), 4.60 (2H, s), 5.30 (2H, s), 6.90 (1H, d), 7.00 (1H, s), 7.15 (1H, s), 7.30 (1H, m), 7.75 (1H, m), 8.50 (1H, d).

LRMS: m/z 274 (M)$^+$

Preparation 22

4-(2-Ethoxybenzamido)-3-ethyl-2-(pyridin-2-yl) methyl-pyrazole-5-carboxamide

A solution of ethoxybenzoyl chloride (2 g, 10.8 mmol) in dichloromethane (5 ml) was added dropwise to a solution of the title compound of preparation 20 (2.4 g, 9.72 mmol) and triethylamine (1.8 ml, 12.96 mmol) in dichloromethane (15 ml) at 0° C. The resultant mixture was stirred at room temperature for 18 hours, then diluted with water (10 ml). The dichloromethane was removed under reduced pressure, the residue redissolved in ethyl acetate (20 ml) and extracted with hydrochloric acid (2N, 10 ml). The combined aqueous acid layers were washed with diethyl ether (20 ml), basified with solid sodium hydrogencarbonate solution to pH 8 and extracted with dichloromethane (3×30 ml). The combined dichloromethane layers were dried over MgSO$_4$, filtered and concentrated under reduced pressure to afford the title compound as a white solid (3.65 g, 95%).

$\delta$(CDCl$_3$): 1.05 (3H,t), 1.60 (3H,t), 2.85 (2H,q), 4.35 (2H,q), 5.20–5.30 (1H,br s), 5.50 (2H,s), 6.70 (1H,br s), 6.90 (1H,d); 7.00–7.10 (2H,m), 7.20–7.25 (1H,m), 7.40–7.50 (1H,m), 7.60–7.70 (1H,m), 8.20 (1H,d), 8.60 (1H,s), 10.45 (1H,s).

LRMS: m/z 394 (M+1)$^+$.

Analysis: Found C, 63.93; H, 5.82; N, 17.75; C$_{21}$H$_{23}$N$_5$O$_3$ requires C, 64.10; H, 5.89; N, 17.80%.

Preparation 23

5-(2-Ethoxyphenyl)-3-ethyl-2-(pyridin-2-yl)methyl-2,6-dihydro-7H-pyrazolo[4,3-d]pyrimidin-7-one Potassium tert-butoxide (4.15 g, 37 mmol) was added portionwise, to a stirred solution of the title compound of preparation 22 (3.64 g, 9.25 mmol) in ethanol (50 ml) under an atmosphere of nitrogen and heated under reflux for 18 hours. The reaction mixture was cooled and the solvent removed under reduced pressure. The residue was partitioned between ethyl acetate (100 ml) and water (50 ml), the layers were separated and the organic layer washed with water (50 ml), brine (50 ml), dried over MgSO$_4$, filtered and concentrated under reduced pressure to afford the title compound as white solid (2.8 g).

$\delta$(CDCl$_3$): 1.30 (3H,t), 1.60 (3H,t), 3.00 (2H,q), 4.30 (2H,q), 5.70 (2H,s), 7.00–7.15 (3H,m), 7.20 (1H,m), 7.40 (1H,m), 7.60 (1H,m), 8.40 (1H,d), 8.60 (1H,s), 10.90 (1H,br s).

LRMS: m/z 376 (M+1)$^+$.

Analysis: Found C, 66.79; H, 5.60; N, 18.35; C$_{21}$H$_{21}$N$_5$O$_2$ requires C, 67.18; H, 5.64; N, 18.65%.

Preparation 24

4-Ethylpiperidine

Prepared by following the procedure described in J. Med. Chem., 1991, 34(5), 1545.

Preparation 25

4-Methoxypiperidine

Prepared by following the procedure described in Chem. Soc. Perkin Trans. 2, 1984, 737.

Preparation 26

3-Azetidinol

Prepared by following the procedure described in J. Med. Chem., 1993, 36(4), 460.

Preparation 27 tert-Butyl (1R,5S)-3-endo -azabicyclo[3.1.0]hex-6-ylcarbamate

Prepared by following the procedure described in European Patent no. 0413455.

Preparation 28

5-[5-(4-tert-Butyloxycarbonylpiperazin-1-ylsulfonyl)-2-n-propoxyphenyl]-3-n-propyl-2-(pyridin-2-yl)methyl-2,6-dihydro-7H-pyrazolo[4,3-d]pyrimidin-7-one Obtained from the title compound of preparation 15 and tert-butyl 1 -piperazinecarboxylate using an analogous method to Example 1 (method B) below, as a white solid (60%).

$\delta$(CDCl$_3$): 0.95 (3H,t), 1.15 (3H,t), 1.40 (9H,s), 1.70–1.80 (2H,m), 1.95–2.10 (2H,m), 2.95–3.10 (6H,m), 3.50 (4H,m), 4.30 (2H,t), 5.70 (2H,s), 7.00–7.25 (3H,m), 7.60 (1H,m), 7.80 (1H,d), 8.60 (1H,d), 8.80 (1H,s), 10.60 (1H,s).

LRMS: m/z 652 (M+1)$^+$.

Analysis: Found C, 57.91; H, 5.70; N, 16.70; C$_{28}$H$_{33}$N$_7$O$_4$S. 0.25C.H$_2$Cl$_2$ requires C, 58.01; H, 5.77; N, 16.76%.

Preparation 29

5-({5-[3-(tert-Butyloxycarbonyl)amino]-1-ethylaminosulfonyl}-2-n-propoxyphenyl)-3-n-propyl-2-(pyridin-2-yl)methyl-2,6-dihydro-7H-pyrazolo [4,3-d]pyrimidin-7-one Obtained from the title compound of preparation 15 and tert-butyl 2-aminoethylcarbamate, using an analogous method to Example 1 (method B) below, as a white solid (45%).

$\delta$(CDCl$_3$): 0.95 (3H,t), 1.15 (3H,t), 1.40 (9H,s), 1.70–1.80 (2H,m), 1.95–2.05 (2H,m), 3.00 (2H,t), 3.15 (2H,m), 3.25 (2H,m), 4.20 (2H,t), 5.05 (1H,br s), 5.65 (1H,br s), 5.70 (2H,s), 7.10 (2H,m), 7.25 (1H,m), 7.65 (1H,m), 7.95 (1H,m), 8.60 (1H,d), 8.80 (1H,s), 10.80 (1H,br s).

LRMS: m/z 626 (M+1)$^+$.

Preparation 30

2-Ethoxypyridine-3-carboxylic acid

A solution of potassium ten-butoxide (44.9 g, 0.40 mol) in absolute ethanol (300 ml) was added slowly to a solution of 2-chloronicotinic acid (30 g, 0.19 mol) in ethanol (100 ml), and the reaction heated in a sealed vessel at 170° C. for 20 hours. The solvent was removed under reduced pressure, the residue dissolved in water (200 ml) and acidified to pH 3 with aqueous hydrochloric acid. The aqueous solution was extracted with dichloromethane (4×200 ml), the combined organic layers were dried over Na$_2$SO$_4$, filtered and concentrated under reduced pressure to afford the title compound as a white solid (27.4 g).

$\delta$ (CDCl$_3$): 1.53 (3H,t), 4.69 (2H,q), 7.13 (1H,m), 8.37 (1H,d), 8.48 (1H,d).

Preparation 31

2-n-Propoxypyridine-3-carboxylic acid

Obtained from 2-chloronicotinic acid and 1-propanol, using an analogous method to preparation 30, as a brown solid (56%).

$\delta$(d$_6$-DMSO): 0.95 (3H,t), 1.60–1.80 (2H,m), 4.30 (2H,t), 7.00 (1H,m), 8.05 (1H,d), 8.30 (1H,m), 12.85 (1H,br s).

LRMS: m/z 182 (M+1)$^+$.

Analysis: Found C, 59.09; H, 5.99; N, 7.71; C$_9$H$_{11}$NO$_3$; 0.1H$_2$O requires C, 59.07; H, 6.17; N, 7.65%.

Preparation 32

2-(2-Methoxyethoxy)pyridine-3-carboxylic acid

Obtained from 2-chloronicotinic acid and 2-methoxyethanol, using an analogous method to preparation 30, as a brown solid (92%).

$\delta$(CDCl$_3$): 3.40 (3H,s), 3.80 (2H,t), 4.70 (2H,t), 7.10 (1H,m), 8.35 (1H,m), 8.45 (1H,m).

LRMS: m/z 198 (M+1)$^+$

Preparation 33

2-Ethoxypyridine-3-carboxylic acid ethyl ester

A suspension of the title compound of preparation 30 (16.4 g, 98 mmol), and cesium carbonate (32 g, 98 mmol) in dimethylformamide (240 ml) were stirred at room temperature for 2 hours. Ethyl iodide (7.85 ml, 98 mmol) was added and the reaction stirred for a further 24 hours. The solvent was removed under reduced pressure and the residue partitioned between aqueous sodium carbonate solution (100 ml) and ethyl acetate (100 ml). The layers were separated and the aqueous layer extracted with ethyl acetate (2×100 ml). The combined organic phases were washed with brine (50 ml), dried over Na$_2$SO$_4$, filtered and concentrated under reduced pressure to afford the title compound as a pale yellow oil (18.0 g).

$\delta$(CDCl$_3$): 1.41 (6H,m), 4.36, (2H,q), 4.48 (2H,q), 6.90 (1H,m), 8.12 (1H,d), 8.28 (1H,d).

Preparation 34

2-n-Propoxypyridine-3-carboxylic acid ethyl ester

Obtained from the title compound of preparation 31, using an analogous method to preparation 33, as a yellow oil (99%).

$\delta$(CDCl$_3$): 1.00 (3H,t), 1.30 (3H,t), 1.70–1.80 (2H,m), 4.20–4.35 (4H,m), 6.80 (1H,m), 8.00 (1H,d), 8.20 (1H,d).

LRMS: m/z 210 (M+1)$^+$.

Preparation 35

2-(2-Methoxyethoxy)pyridine-3-carboxylic acid ethyl ester

Obtained from the title compound of preparation 32, using an analogous method to preparation 33, as a light brown oil (98%).

δ(CDCl$_3$): 1.35 (3H,t), 3.45 (3H,s), 3.75 (2H,t), 4.35 (2H,q), 4.55 (2H,t), 6.90 (1H,m), 8.15 (1H,d), 8.25 (1H,m).

LRMS: m/z 226 (M+1)$^+$.

Analysis: Found C, 58.36; H, 6.74; N, 6.04; C$_{11}$H$_{15}$NO$_4$ requires C, 58.66; H, 6.71; N, 6.22%.

Preparation 36

2-Ethoxypyridine-5-nitro-3-carboxylic acid ethyl ester

Ammonium nitrate (5.36 g, 66 mmol) was added portionwise to an ice-cooled solution of the title compound of preparation 33 (4.66 g, 22.3 mmol) in trifluoroacetic anhydride (50 ml) and the reaction stirred for 18 hours at room temperature. The reaction mixture was carefully poured onto ice water (200 ml) and the resulting suspension stirred for 1 hour. The precipitate was filtered off, washed with water and dried under suction to afford the title compound (3.29 g).

δ(CDCl$_3$): 1.41 (3H,t), 1.48 (3H,t), 4.41 (2H,q), 4.62 (2H,q), 8.89 (1H,s), 9.16 (1H,s).

Preparation 37

5-Nitro-2-n-propoxypyridine-3-carboxylic acid ethyl ester

Obtained from the title compound of preparation 34, using an analogous method to preparation 36, as a cream solid (99%).

δ(CDCl$_3$): 1.05 (3H,t), 1.20 (3H,t), 1.80–1.95 (2H,m), 4.40 (2H,q), 4.50 (2H,t), 8.90 (1H,s), 9.15 (1H,s).

Preparation 38

2-(2-Methoxyethoxy)pyridine-5-nitro-3-carboxylic acid ethyl ester

Ammonium nitrate (10.57 g, 0.13 mol) was added portionwise to an ice-cooled solution of the title compound of preparation 35 (14.80 g, 0.07 mol) in trifluoroacetic anhydride (150 ml) in a large 1 liter flask, equipped with an air condenser. The reaction mixture was stirred for 3 hours at room temperature, carefully poured into ice water (120 g) and the resulting solution was extracted with dichloromethane (3×150 ml). The combined organic layers were dried over MgSO$_4$, filtered and concentrated under reduced pressure. The resultant orange oil was dried under vacuum to give a solid which was triturated with diethyl ether and filtered to afford the title compound as a white solid. The filtrate was concentrated under reduced pressure and the residue purified by column chromatography on silica gel eluting with a gradient system of dichloromethane:methanol (99:1 to 97:3) to afford further title compound (11.5 g total).

δ(CDCl$_3$): 1.40 (3H,t), 3.40 (3H,s), 3.80 (2H,t), 4.40 (2H,q), 4.70 (2H,t), 8.90 (1H,s), 9.15 (1H,s). LRMS: m/z 271 (M+1)$^+$.

Analysis: Found C, 48.78; H, 5.13; N, 10.29; C$_{11}$H$_{14}$N$_2$O$_6$ requires C, 48.89; H, 5.22; N, 10.37%.

Preparation 39

5-Amino-2-ethoxypyridine-3-carboxylic acid ethyl ester

A mixture of the title compound of preparation 36 (5.3 g, 22 mmol) and Raney nickel (2.50 g) in ethanol (150 ml) was hydrogenated for 18 hours at 345 kPa (50 psi) and 50° C., then cooled and filtered. The filter pad was washed with ethanol (150 ml) and the filtrate was concentrated under reduced pressure. The residue was triturated with dichloromethane, the resulting solid filtered and dried to afford the title compound as a tan coloured solid (4.56 g).

δ(CDCl$_3$): 1.39 (6H,m), 3.41 (2H,s), 4.35 (4H,m), 7.55 (1H,s), 7.78 (1H,s).

LRMS: m/z 211 (M+1)$^+$.

Found: C, 57.12; H, 6.79; N, 12.98. C$_{10}$H$_{14}$N$_2$O$_3$ requires C, 57.13; H, 6.71; N, 13.33%.

Preparation 40

5-[(Dimethylamino)sulfonyl]-2-ethoxypyridine-3-carboxylic acid ethyl ester

A solution of the title compound of preparation 39 (1.5 g, 7.14 mmol) in acetic acid (30 ml) and concentrated hydrochloric acid (30 ml) was cooled to −20° C. and sodium nitrite (740 mg, 10.7 mmol) added. The reaction mixture was warmed to 0° C. over 2 hours, then cooled back to −20° C. Sulfur dioxide (17 ml) was added followed by a suspension of copper(II) chloride (2.78 g, 20.7 mmol) in water (3 ml) and acetic acid (25 ml). The reaction mixture was warmed to 0° C., stirred for 30 minutes, then warmed to room temperature and stirred for 2 hours. The reaction mixture was poured onto ice (25 g) and extracted with dichloromethane (3×50 ml). The combined organic layers were dried over MgSO$_4$, filtered, concentrated under reduced pressure and the residue was azeotroped with toluene. The resultant solid was dissolved in ethanol (10 ml), dimethylamine (5.1 ml, 28.54 mmol) was added and the mixture stirred at room temperature for 18 hours. The solvent was removed under reduced pressure and the residue dissolved in dichloromethane (20 ml), washed with water (10 ml), dried over MgSO$_4$, filtered and concentrated under reduced pressure. The residue was purified by column chromatography on silica gel eluting with a gradient system of dichloromethane:methanol (100:0 to 99:1) to afford the title compound as a white solid (1.28 g).

δ(CDCl$_3$): 1.35–1.60 (6H,m), 2.80 (6H,s), 4.40 (2H,q), 4.60 (2H,q), 8.40 (1H,s), 8.70 (1H,s).

LRMS: m/z 303 (M+1)$^+$.

Found: C, 47.69; H, 5.99; N, 9.13. C$_{12}$H$_{18}$N$_2$O$_5$S requires C, 47.67; H, 6.00; N, 9.27%.

Preparation 41

5-[(Dimethylamino)sulfonyl]-2-ethoxypyridine-3-carboxylic acid

Aqueous sodium hydroxide solution (15 ml, 1N) was added dropwise to a solution of the title compound of preparation 40 (1.25 g, 4.13 mmol) in ethanol (15 ml) and the reaction stirred at room temperature for 2 hours. The solvent was removed under reduced pressure, the residue suspended in water (15 ml) and acidified to pH 3 with hydrochloric acid (6N). The resultant white suspension was extracted with ethyl acetate (3×30 ml), the combined organic layers washed with brine (100 ml), dried over MgSO$_4$, filtered and concentrated under reduced pressure to give a white solid (940 mg).

δ(CDCl$_3$): 1.60 (3H,t), 2.80 (6H,s), 4.80 (2H,q), 8.80 (2H,s), 10.10–10.30 (1H,br s).

LRMS: m/z 275 (M+1)$^+$.

Found: C, 43.56; H, 5.09; N, 10.04. C$_{10}$H$_{14}$N$_2$O$_5$S requires C, 43.79; H, 5.14; N, 10.21%.

Preparation 42

5-[(Dimethylamino)sulfonyl]-2-ethoxypyridine-3-carbonyl chloride

Oxalyl chloride (0.59 ml, 6.7 mmol) was added dropwise to a cooled solution of the title compound of preparation 41

(920 mg, 3.35 mmol) in dichloromethane (15 ml) followed by dimethylformamide (1 drop) and the resultant mixture stirred at room temperature for 18 hours. The solvent was removed under reduced pressure, azeotroped with toluene, then triturated with hexane and filtered to afford the title compound as a white solid (845 mg).

δ(CDCl$_3$): 1.50 (3H,t), 2.80 (6H,s), 4.60 (2H,q); 8.60 (1H,s), 8.75 (1H,s).

LRMS: m/z 291 (M+1)$^+$.

Found: C, 40.93; H, 4.33; N, 9.54. C$_{10}$H$_{13}$ClN$_2$O$_4$S requires C, 41.03; H, 4.48; N, 9.57%.

Preparation 43

4-{5-[(N,N-Dimethylamino)sulfonyl]-2-ethoxy-pyridin-3-ylcarboxamido}-3-n-propyl-2-(pyridin-2-yl)methyl-pyrazole-5-carboxamide A mixture of the title compound of preparation 42 (200 mg, 0.68 mmol) and title compound of preparation 21 (177 mg, 0.68 mmol) in pyridine (5 ml) was stirred for 18 hours at room temperature under an atmosphere of nitrogen. The solvent was removed under reduced pressure and the residue was purified by column chromatography on silica gel eluting with a gradient system of dichloromethane:methanol (99:1 to 98:2) to afford the title compound as a white solid (235 mg).

δ(CDCl$_3$): 0.80 (3H,t), 1.40 (2H,m), 1.55 (3H,t), 2.70 (6H,s), 2.80 (2H,t), 4.75 (2H,q), 5.20–5.30 (1H,br s), 5.40 (2H,s), 6.60–6.70 (1H,br s), 6.90 (1H,d), 7.20 (1H,m), 7.60 (1H,m), 8.55 (1H,m), 8.60 (1H,s), 8.80 (1H,s), 10.50 (1H,s).

LRMS: m/z 516 (M+1)$^+$.

Found: C, 49.46; H, 5.29; N, 17.16. C$_{23}$H$_{29}$N$_7$O$_5$S 0.7CH$_2$Cl$_2$ requires C, 49.50; H, 5.33; N, 17.05%.

Preparation 44

2-Ethoxypyridine-5-nitro-3-carboxylic acid

Aqueous sodium hydroxide solution (4 ml, 5N) was added dropwise to a solution of the title compound of preparation 36 (5.1 g, 20 mmol) in ethanol (100 ml) and stirred at room temperature for 18 hours. The solvent was removed under reduced pressure, the residue suspended in water (50 ml) and acidified to pH 3 with hydrochloric acid (6N). This aqueous solution was extracted with ethyl acetate (3×100 ml), the combined organic layers washed with brine (100 ml), dried over Na$_2$SO$_4$, filtered and evaporated under reduced pressure to give a beige solid. The crude product was recrystallised from ethyl acetate:hexane to afford the title compound as beige crystals (3.32 g).

δ(CDCl$_3$): 1.55 (3H,t), 4.78 (2H,q), 9.17 (1H,s), 9.23 (1H,s).

Preparation 45

5-Nitro-2-n-propoxypyridine-3-carboxylic acid

Aqueous sodium hydroxide solution (100 ml, 1N) was added dropwise to a solution of the title compound of preparation 37 (12 g, 47.8 mmol) in ethanol (100 ml) and stirred at room temperature for 2 hours. The solvent was removed under reduced pressure, the residue suspended in water (100 ml) and acidified to pH 4 with hydrochloric acid (6N). This aqueous solution was cooled to 0° C. and a white precipitate formed. After cooling for 2 hours the solid was filtered and dried to afford the title compound as a white solid (7.8 g).

δ(CDCl$_3$): 1.10 (3H,t), 1.95 (2H,m), 4.65 (2H,t), 9.15 (1H,s), 9.20 (1H,s).

Preparation 46

2-(2-Methoxyethoxy)pyridine-5-nitro-3-carboxylic acid

Aqueous sodium hydroxide solution (40 ml, 1N) was added dropwise to a solution of the title compound of preparation 38 (4 g, 14.8 mmol) in dioxan (40 ml) and stirred at room temperature for 2 hours. The solvent was removed under reduced pressure, the residue suspended in water (40 ml) and acidified to pH 3 with hydrochloric acid (6N). The resultant white solid was extracted with dichloromethane (3×50 ml), the combined organic layers dried over MgSO$_4$, filtered and concentrated under reduced pressure to afford the title compound as a beige solid (2.61 g).

δ(CDCl$_3$): 3.45 (3H,s), 3.80 (2H,t), 4.80 (2H,t), 9.15 (1H,s), 9.20 (1H,s).

LRMS: m/z 243 (M+1)$^+$.

Found: C, 44.11; H, 4.04; N, 11.46. C$_9$H$_{10}$N$_2$O$_6$ requires C, 44.63; H, 4.16; N, 11.57%.

Preparation 47

4-(2-Ethoxy-5-nitro-pyridin-3-ylcarboxamido)-3-n-propyl-2-(pyridin-2-yl)methyl-pyrazole-5-carboxamide Oxalyl chloride (2.73 ml, 31 mmol) was added dropwise to a suspension of the title compound of preparation 44 (3.31 g, 15.7 mmol) in dichloromethane (50 ml) followed by dimethylformamide (2 drops) and stirred at room temperature for 3 hours. The solvent was removed under reduced pressure and azeotroped with hexane to give a white solid. A solution of the acid chloride in dichloromethane (20 ml) was added dropwise to a suspension of the title compound of preparation 21 (4.06 g, 15.7 mmol) and triethylamine (4.37 ml, 31 mmol) in dichloromethane (80 ml) and stirred at room temperature for 20 hours. The solvent was removed under reduced pressure and the residue partitioned between aqueous sodium hydrogencarbonate solution (200 ml) and dichloromethane (300 ml). The layers were separated, and the aqueous layer extracted with dichloromethane (2×300 ml). The combined organic layers were washed with brine (300 ml), dried over Na$_2$SO$_4$, filtered and concentrated under reduced pressure to give a purple solid. The solid was triturated with diethyl ether and dried under suction to afford the title compound as an off-white solid (6.26 g).

δ(CDCl$_3$): 0.85 (3H,t), 1.45 (2H,m), 1.60 (3H,t), 2.90 (2H,t), 4.85 (2H,q), 5.30 (1H,s), 5.50 (2H,s), 6.70 (1H,s), 6.95 (1H,d), 7.25 (1H,m), 7.65 (1H,m), 8.60 (1H,d), 9.15 (1H,s), 9.30 (1H,s), 10.60 (1H,s).

LRMS: m/z 454 (M+1).

Found: C, 55.42; H, 5.05; N, 21.49. C$_{21}$H$_{23}$N$_7$O$_5$ requires C, 55.62; H, 5.11; N, 21.62%.

Preparation 48

4-(5-Nitro-2-n-propoxy-pyridin-3-ylcarboxamido)-3-n-propyl-2-(2-pyridin-2-yl)methyl-pyrazole-5-carboxamide The title compound of preparation 45 (500 mg, 2.21 mmol), 1-hydroxybenzotriazole hydrate (299 mg, 2.21 mmol), 1-(3-dimethylaminopropyl)-3-ethylcarbodiimide hydrochloride (424 mg, 2.21 mmol) and N-ethyldiisopropylamine (0.77 ml, 4.42 mmol) were added to a stirred solution of the title compound of preparation 21 (573 mg, 2.21 mmol) in dry dichloromethane (15 ml) at 10° C. The reaction mixture was warmed to room temperature and stirred for 18 hours. The resultant mixture was washed with water (10 ml), aqueous hydrochloric acid (0.5N, 10 ml), and saturated aqueous sodium hydrogencarbonate (10 ml), dried over $MgSO_4$, filtered and concentrated under reduced pressure. The residue was purified by column chromatography on silica gel eluting with a gradient system of dichloromethane:methanol (99:1 to 98:2) to afford the title compound as a white solid (590 mg).

δ($CDCl_3$): 0.80 (3H,t), 1.00 (3H,t), 1.35–1.45 (2H,m), 1.95–2.05 (2H,m), 2.85 (2H,t), 4.70 (2H,t), 5.20–5.30 (1H, br s), 5.45 (2H,s), 6.60–6.75 (1H,br s), 6.90 (1H,d), 7.20 (1H,m), 7.65 (1H,m), 8.60 (1H,m), 9.10 (1H,s), 9.30 (1H,s), 10.45 (1H,s).

LRMS: m/z 468 (M+1)$^+$.

Found: C, 55.84; H, 5.33; N, 20.68. $C_{22}H_{25}N_7O_5$ 0.1$CH_2Cl_2$. requires C, 55.78; H, 5.37; N, 20.60%.

Preparation 49

4-[2-(2-Methoxyethoxy)-5-nitro-pyridin-3-ylcarboxamido]-3-n-propyl-2-(2-pyridin-2-yl)methyl-pyrazole-5-carboxamide Obtained from the title compound of preparation 46 and the title compound of preparation 21, using an analogous method to preparation 48, as a white solid (58%).

δ($CDCl_3$): 1.10 (3H,t), 2.90 (2H,q), 3.40 (3H,s), 4.00 (2H,t), 4.90 (2H,t), 5.20–5.35 (1H,br s), 5.50 (2H,s), 6.65–6.75 (1H,br s), 6.90 (1H,d), 7.20 (1H,m), 7.70 (1H,t), 8.60 (1H,d), 9.15 (1H,s), 9.30 (1H,s), 10.50 (1H,s).

LRMS: m/z 470 (M+1)$^+$.

Found: C, 53.41; H, 4.90; N, 20.65. $C_{21}H_{23}N_7O_6$. requires C, 53.72; H, 4.94; N, 20.89%.

Preparation 50

4-[5-Amino-2-ethoxy-pyridin-3-ylcarboxamido]-3-n-propyl-2-(2-pyridin-2-yl)methyl-pyrazole-5-carboxamide A stirred mixture of the title compound of preparation 47 (5 g, 11 mmol) and Raney nickel (2.5 g) in ethanol (150 ml) was hydrogenated for 3 hours at 345 kPa (50 psi) and 50° C., and then a further 72 hours at room temperature. The resultant mixture was filtered through ARBOCEL (registered trademark of J. Rettenmaier & Sohne GmbH & Co., W-7091 Holzmuhle uber Ellwangen/Jagst, Germany), and the filtrate concentrated under reduced pressure to give a pale yellow solid. The residue was purified by column chromatography on silica gel eluting with a gradient system of dichloromethane:methanol (99:1 to 95:5). The resultant solid was triturated with diethyl ether to afford the title compound as a beige solid (4.4 g).

δ($CDCl_3$): 0.78 (3H,t), 1.43 (2H,m), 1.52 (3H,t), 2.82 (2H,t), 3.49 (2H,s), 4.59 (2H,q), 5.30 (1H,s), 5.46 (2H,s), 6.70 (1H,s), 6.93 (1H,d), 7.22 (1H,m), 7.65 (1H,m), 7.78 (1H,s), 7.94 (1H,s), 8.58 (1H,d), 10.53 (1H,s).

Found: C, 59.42; H, 5.96; N, 22.98. $C_{21}H_{25}N_7O_3$ requires C, 59.56; H, 5.95; N, 23.15%.

Preparation 51

4-[5-Amino-2-n-propoxy-pyridin-3-ylcarboxamido]-3-n-propyl-2-(2-pyridin-2-yl)methyl-pyrazole-5-carboxamide Obtained from the title compound of preparation 48, using an analogous method to preparation 50, as a pale yellow solid (86%).

δ($CDCl_3$): 0.80 (3H,t), 1.00 (3H,t), 1.40–1.50 (2H,m), 1.90–2.00(2H,m), 2.80 (2H,t), 3.50 (2H,s), 4.45 (2H,t), 5.20–5.35 (1H,br s), 5.45 (2H,s), 6.60–6.75 (1H,br s), 6.95 (1H,d), 7.20 (1H,m), 7.65 (1H,m), 7.80 (1H,s), 7.90 (1H,s), 8.60 (1H,d), 10.45 (1H,s).

Found: C, 57.97; H, 6.26; N, 21.18. $C_{22}H_{27}N_7O_3$ 0.3$CH_2Cl_2$ requires C, 57.85; H, 6.01; N, 21.18%.

Preparation 52

4-[5-Amino-2-(2-methoxyethoxy)-pyridin-3-ylcarboxamido]-3n-propyl-2-(2-pyridin-2-yl)methyl-pyrazole-5-carboxamide Obtained from the title compound of preparation 49, using an analogous method to preparation 39, as a grey solid (100%).

δ($CDCl_3$): 1.05 (3H,t), 2.80 (2H,q), 3.40 (3H,s), 3.40–3.60 (2H,br s), 3.90 (2H,t), 4.65 (2H,t), 5.30–5.40 (1H,br s), 5.50 (2H,s), 6.60–6.80 (1H,br s), 6.90 (1H,s), 7.20 (1H,m), 7.65 (1H,m), 7.80 (1H,s), 7.95 (1H,s), 8.60 (1H,d), 10.50 (1H,s).

LRMS: m/z 440 (M+1)$^+$.

Found: C, 56.47; H, 5.82; N, 21.40. $C_{21}H_{25}N_7O_4$ 0.4$H_2O$. Requires C, 56.47; H, 5.82; N, 21.95%.

Preparation 53

5-(5-Amino-2-ethoxypyridin-3-yl)-3-n-propyl-2-(pyridin-2-yl)methy-2,6-dihydro-7H-pyrazolo[4,3-d]pyrimidin-7-one Potassium tert-butoxide (2.32 g, 20 mmol) was added carefully to a suspension of the title compound of preparation 50 (2.11 g, 5 mmol) and 4 Å molecular sieves in ethanol (50 ml) and the reaction heated under reflux for 18 hours. The cooled mixture was filtered through ARBOCEL®, the filtrate concentrated under reduced pressure and the residue partitioned between aqueous hydrochloric acid (30 ml, 1N) and ethyl acetate (30 ml). The layers were separated, the aqueous layer extracted with ethyl acetate (2×30 ml), and the combined organic layers washed with brine (30 ml), dried over $Na_2SO_4$, filtered and concentrated under reduced pressure. The residual brown oil was purified by column chromatography on silica gel eluting with a gradient system of dichloromethane:methanol (100:0 to 96:4) to afford the title compound as a pale yellow solid (1.22 g).

δ($CDCl_3$): 0.95 (3H,t), 1.50 (3H,t), 1.60 (2H,m), 2.95 (2H,t), 3.60 (2H,s), 4.50 (2H,q), 5.70 (2H,s), 7.05 (1H,d), 7.20 (1H,m), 7.60 (1H,m), 7.80 (1H,s), 8.15 (1H,d), 8.60 (1H,s), 11.05(1H,s).

Found: C, 61.92; H, 5.69; N, 23.95. $C_{21}H_{23}N_7O_2$ requires C, 62.21; H, 5.72; N, 24.18%.

Preparation 54

5-(5-Amino-2-n-propoxypyridin-3-yl) 3-n-propyl-2-(pyridin-2-yl)methyl-2,6-dihydro-7H-pyrazolo[4,3-d]pyrimidin-7-one Potassium tert-butoxide (441 mg, 3.9 mmol) was added carefully to a suspension of the title compound of preparation 51 (430 mg, 0.98 mmol) in 1-propanol (15 ml) and the reaction heated under reflux for 18 hours. The solvent was removed under reduced pressure, the residue dissolved in water (10 ml), acidified to pH 5 with hydrochloric acid (2N) and extracted with dichloromethane (3×15 ml). The combined organic layers were dried over $MgSO_4$, filtered and concentrated under reduced pressure. The residual brown oil was purified by column chromatography on silica gel eluting with a solvent system of dichloromethane:methanol (97:3) to afford the title compound as a yellow solid (237 mg).

δ(CDCl$_3$): 0.95 (3H,t), 1.10 (3H,t), 1.70–1.80 (2H,m), 1.85–2.00 (2H,m), 2.95 (2H,t), 3.60 (1H,s), 4.45 (2H,t), 5.65 (2H,s), 7.05 (1H,d), 7.20–7.25 (1H,m), 7.60 (1H,t), 7.80 (1H,s), 8.20 (1H,s), 8.60 (1H,d), 11.10 (1H,s).

LRMS: m/z 420 (M+1)$^+$.

Preparation 55

5-[5-Amino-2-(2-methoxyethoxy)pyridin-3-yl]-3-ethyl-2-(pyridin-2-yl)methyl-2,6-dihydro-7H-pyrazolo[4,3-d]pyrimidin-7-one Potassium tert-butoxide (6.58 g, 33 mmol) was added carefully to a suspension of the title compound of preparation 52 (2.90 g, 6.60 mmol) in 2-methoxyethanol (70 ml), the mixture heated under reflux for 18 hours and then cooled. The solvent was removed under reduced pressure and the residue purified by column chromatography on silica gel eluting with a gradient system of dichloromethane:methanol (98:2 to 95:5) to afford the title compound as a white solid (2.20 g).

δ(CDCl$_3$): 1.30 (3H,t), 3.00 (2H,q), 3.55 (3H,s), 3.60 (2H,s), 3.80 (2H,t), 4.60 (2H,t), 5.65 (2H,s), 7.05 (1H,d), 7.20 (1H,m), 7.60 (1H,m), 7.80 (1H,s), 8.10 (1H,s), 8.60 (1H,d), 11.15 (1H,s).

LRMS: m/z 422 (M+1)$^+$.

Found: C, 59.10; H, 5.44; N, 22.86. C$_{21}$H$_{23}$N$_7$O$_3$ requires C, 59.09; H, 5.57; N, 22.97%.

Preparation 56

5-[5-Chlorosulfonyl-2-(2-methoxyethoxy)pyridin-3-yl]-3-ethyl-2-(pyridin-2-yl)methyl-2,6-dihydro-7H-pyrazolo[4,3-d]pyrimidin-7-one A solution of the title compound of preparation 55 (1.5 g, 7.14 mmol) in acetic acid (30 ml) and concentrated hydrochloric acid (30 ml) was cooled to −20° C. and sodium nitrite (714 mg, 10.35 mmol) added. The reaction mixture was warmed to 0° C. over 2 hours, then cooled back to −20° C. Sulfur dioxide (20 ml) was added followed by a suspension of copper(II) chloride (2.09 g, 15.52 mmol) in water (3 ml). The reaction mixture was warmed to 0° C., stirred for 30 minutes, then warmed to room temperature and stirred for 2 hours. The reaction mixture was poured onto ice (60 g) and the resulting suspension extracted with dichloromethane (5×5 ml). The combined organic layers were dried over MgSO$_4$, filtered and concentrated under reduced pressure. The residue was stirred in diethyl ether (50 ml) and filtered to afford the title compound as a beige solid (2.2 g).

δ(CDCl$_3$): 1.30 (3H,t), 3.10 (2H,q), 3.60 (3H,s), 3.90 (2H,t), 4.85 (2H,t), 5.70 (2H,s), 7.10 (1H,d), 7.20 (1H,m), 7.65 (1H,m), 8.60 (1H,s), 8.90 (1H,s), 9.25 (1H,s), 10.75 (1H,s).

LRMS: m/z 505 (M+1)$^+$.

Found: C, 49.11; H, 4.13; N, 16.02. C$_{21}$H$_{21}$ClN$_6$O$_5$S 0.6H$_2$O requires C, 48.90; H, 4.34; N, 16.29%.

Preparation 57

4-Benzyl-tetrahydro-1,4-thiazine 1,1-dioxide

Divinyl sulphone (0.8 ml, 10 mmol) was added to a solution of benzylamine (1.09 ml, 10 mmol) in ethanol (4 ml) and heated under reflux for 2 hours. The solvent was removed under reduced pressure, the residue dissolved in dichloromethane (30 ml) and washed with saturated aqueous sodium hydrogencarbonate solution (15 ml), dried over MgSO$_4$, filtered and concentrated under reduced pressure. The residue was purified by column chromatography on silica gel eluting with a gradient system of dichloromethane:methanol (100:0 to 99:1) to afford the title compound as a yellow oil (0.9 g).

δ(CDCl$_3$): 3.00 (4H,m), 3.05 (4H,m), 3.65 (2H,s), 7.25–7.40 (5H,m).

LRMS: m/z 226 (M+1)$^+$.

Preparation 58

Tetrahydro-1,4-thiazine 1,1-dioxide acetate

A stirred mixture of the title compound of preparation 57 (250 mg, 1.1 mmol) and 10% palladium on charcoal (30 mg) in acetic acid (5 ml) was hydrogenated for 18 hours at 207 kPa (30 psi) and room temperature. Water (5 ml) was added and the mixture filtered through ARBOCEL to remove the catalyst. The filtrate was concentrated under reduced pressure to give the title compound as a white solid (240 mg).

δ(CDCl$_3$): 1.85 (3H,s), 2.95 (4H,m), 3.05 (4H,m).

LRMS: m/z 226 (M+1)$^+$.

Preparation 59

5-(2-Ethoxy-5-{3-[(2,2,2-trifluoroacetyl)ethylamino]-1-azetidinesulfonyl}pyridin-3-yl)-3-n-propyl-2-(pyridin-2-yl)methyl-2,6-dihydro-7H-pyrazolo[4,3-d]pyrimidin-7-one A solution of the title compound of preparation 53 (613 mg, 1.51 mmol) in acetic acid (6.25 ml) and concentrated hydrochloric acid (10 ml) was cooled to −20° C. and sodium nitrite (203 mg, 3.03 mmol) added. The reaction mixture was warmed to 0° C. over 2 hours, then cooled back to −20° C. Sulfur dioxide (11 ml) was added followed by a suspension of copper(II) chloride (606 mg, 4.50 mmol) in water (2 ml) and acetic acid (5 ml). The reaction mixture was warmed to 0° C., stirred for 30 minutes, then warmed to room temperature and stirred for 1 hour. The reaction mixture was poured into ice water (95 ml) and extracted with dichloromethane (3×50 ml). The combined organic layers were washed with brine (50 ml), dried over Na$_2$SO$_4$, filtered and concentrated under reduced pressure. The resultant oil was triturated with diethyl ether and filtered to give a white solid. This solid was dissolved in ethanol (40 ml), and a solution of N-(3-azetidinyl)-N-ethyl-2,2,2-trifluoroacetamide (280 mg, 1.42 mmol; J. Med. Chem., 1993, 36, 9, 808) in ethanol (5 ml) was added and stirred for 18 hours at room temperature. The solvent was removed under reduced pressure and the residue suspended in saturated sodium hydrogencarbonate solution (20 ml) and extracted with ethyl acetate (3×30 ml). The combined organic layers were washed with brine (3×20 ml), dried over MgSO$_4$, filtered and concentrated under reduced pressure. The residue was purified by column chromatography on silica gel eluting with a gradient system of dichloromethane:methanol (100:0 to 98:2). The resultant oil was suspended in diethyl ether and concentrated under reduced pressure (×3) to afford the title compound as a white solid (450 mg).

δ(CDCl$_3$): 0.95 (3H,t), 1.20 (3H,t), 1.50–1.65 (5H,m), 1.65–1.80 (2H,m), 3.00 (2H,t), 3.45 (2H,t), 4.10 (3H,m), 4.80 (2H,q), 5.70 (2H,s), 7.10 (1H,d), 7.20 (1H,m), 7.60 (1H,m) 8.60 (1H,m), 8.75 (1H,s), 9.10 (1H,s), 10.65 (1H,br s).

LRMS: m/z 649 (M+1)$^+$.

Preparation 60

5-{5-[(1R,5S)-6-exo-[(tert-Butoxycarbonyl)amino]-3-azabicyclo[3.1.0]hex-3-ylsulfonyl]-2-ethoxy-pyridin-3-yl}-3-n-propyl-2-(pyridin-2-yl)methyl-2,6-dihydro-7H-pyrazolo[4,3-d]pyrimidin-7-one Obtained from the title compound of preparation 53 and tert-butyl (1R,5R)-3-azabicyclo[3.1.0]hex-6-ylcarbamate (EP 413 455), by an analogous method to preparation 59, as a white solid (45%).

δ(CDCl$_3$): 0.95 (3H,t), 1.40 (9H,s), 1.60 (3H,t), 1.65–1.80 (4H,m), 2.50 (1H,s), 3.00 (3H,t), 3.20 (2H,d), 3.70 (2H,d), 4.50–4.65 (1H,br s), 4.75 (1H,q), 5.70 (2H,s), 7.10 (1H,d), 7.20 (1H,m), 7.60 (1H,m), 8.60 (1H,m), 8.65 (1H,s), 9.00 (1H,s), 10.65 (1H,br s).

LRMS: m/z 651 (M+1)$^+$.

Found: C, 57.61; H, 6.10; N, 16.64. $C_{31}H_{38}N_8O_6S$ 0.1$C_6H_{14}$ requires C, 57.56; H, 6.02; N, 17.00%.

Synthesis of the Compounds of Formulae IA and IB

Example 1

5-[5-(N,N-Dimethylaminosulfonyl)-2-n-propoxyphenyl]-3-n-propyl-2-(pyridin-2-yl)methyl-2,6-dihydro-7H-pyrazolo[4,3-d]pyrimidin-7-one The title compound of preparation 15 (250 mg, 0.60 mmol) was dissolved in chlorosulfonic acid (2 ml, 30 mmol) and thionyl chloride (0.50 ml, 6.90 mmol) was added slowly. The resultant mixture was stirred at room temperature for 18 hours. The reacting mixture was quenched by pouring onto ice and the white precipitate which formed was filtered and dried under vacuum. The resultant solid was suspended in ethanol (10 ml), dimethylamine (0.14 ml, 3.0 mmol) added and the mixture was stirred at room temperature for 18 hours. The solvent was removed under reduced pressure, the residue dissolved in dichloromethane (30 ml) and washed with saturated aqueous sodium hydrogencarbonate solution (15 ml), dried over MgSO$_4$, filtered and concentrated under reduced pressure. The residue was purified by column chromatography on silica gel eluting with a solvent system of dichloromethane:methanol (98:2) to afford the title compound as a white solid (209 mg).

δ(CDCl$_3$): 0.95 (3H,t), 1.20 (3H,t), 1.75 (2H,q), 2.05 (2H,q), 2.80 (6H,s), 3.00 (2H,t), 4.25 (2H,t), 5.70 (2H,s), 7.10 (1H,d), 7.35–7.15 (2H,m), 7.60 (1H,m), 7.85 (1H,m), 8.60 (1H,d), 8.80 (1H,s), 10.60 (1H,br s).

LRMS: m/z 511 (M+1)$^+$.

Analysis: Found C, 57.57; H, 5.83; N, 15.99; $C_{25}H_{30}N_6O_4S$. 0.15$CH_2Cl_2$. requires C, 57.72; H, 5.84; N, 16.06%.

Examples 2 to 11

The compounds of the following tabulated examples of the general formula:

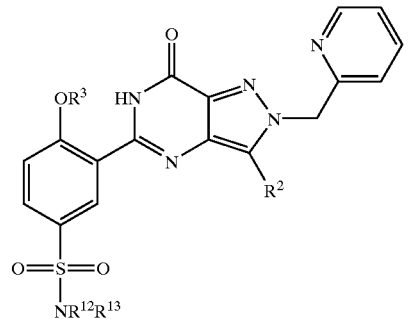

were prepared by the method of example 1 (method A) using the corresponding pyrazolo[4,3-d]pyrimidin-7-one and the appropriate amine. Alternatively, the compounds were prepared using the method of example 1, except that 1.2 equivalents of the appropriate amine and 2 equivalents of triethylamine were used (method B).

| Example No. | R$^3$ | R$^2$ | NR$^{12}$R$^{13}$ | Method | Data |
|---|---|---|---|---|---|
| 2 | Propyl | Propyl | NH—CH$_2$CH$_2$—O—CH$_3$ | A | δ (CDCl$_3$): 0.95 (3H, t), 1.15 (3H, t), 1.65–1.80 (2H, m), 1.95–2.10 (2H, m), 3.00 (2H, t), 3.20 (2H, q), 3.30 (3H, s), 3.45 (2H, m), 4.20 (2H, t), 4.90 (1H, t), 5.70 (2H, s), 7.05 (1H, d), 7.15 (1H, d), 7.25 (1H, m), 7.60 (1H, m), 7.95 (1H, m), 8.60 (1H, d), 8.85 (1H, s), 10.60 (1H, br s). LRMS: m/z 541 (M + 1)$^+$. Analysis: Found C, 57.29; H, 5.98; N, 15.29; $C_{26}H_{32}N_6O_5S$. 0.1$CH_2Cl_2$. requires C, 57.19; H, 5.74; N, 15.33%. |
| 3 | Propyl | Propyl | morpholine (O, N ring) | A | δ (CDCl$_3$): 0.95 (3H, t), 1.15 (3H, t), 1.75 (2H, m), 2.05 (2H, m), 2.98 (2H, t), 3.00–3.10 (4H, m), 3.70–3.80 (4H, m), 4.25 (2H, t), 5.70 (2H, s), 7.05 (1H, d), 7.10–7.30 (2H, m), 7.60 (1H, m), 7.85 (1H, m), 8.60 (1H, d), 8.80 (1H, s), 10.60 (1H, br s). LRMS: m/z 553 (M + 1)$^+$. Analysis: Found C, 57.79; H, 5.75; N, 14.89; $C_{27}H_{32}N_6O_5S$. requires C, 58.68; H, 5.84; N, 15.20%. |

-continued

| Example No. | R³ | R² | NR¹²R¹³ | Method | Data |
|---|---|---|---|---|---|
| 4 | Ethyl | Ethyl | 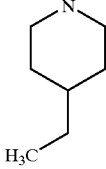 | B | δ (CDCl₃): 0.85 (3H, t), 1.00–1.20 (1H, m), 1.20–1.40 (7H, m), 1.60 (3H, m), 1.70 (2H, m), 2.30 (2H, t), 3.00 (2H, q), 3.80 (2H, m), 4.40 (2H, q), 5.70 (2H, s), 7.05 (1H, d), 7.15 (1H, d), 7.20 (1H, m), 7.60 (1H, m), 7.80 (1H, m), 8.60 (1H, d), 8.80 (1H, s), 10.65 (1H, br s). LRMS: m/z 551 (M + 1)⁺. Analysis: Found C, 60.37; H, 6.29; N, 14.83; C₂₈H₃₄N₆O₄S. 0.35H₂O. requires C, 60.38; H, 6.28; N, 15.09%. |
| 5 | Propyl | Ethyl | 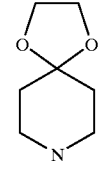 | B | δ (CDCl₃): 0.95 (3H, t), 1.30 (3H, m), 1.80 (4H, m), 2.00 (2H, m), 3.00 (2H, q), 3.20 (4H, m), 3.90 (4H, s), 4.20 (2H, t), 5.70 (2H, s), 7.10 (1H, d), 7.15 (1H, d), 7.20 (1H, m), 7.60 (1H, m), 7.80 (1H, m), 8.60 (1H, d), 8.80 (1H, s), 10.60 (1H, s). LRMS: m/z 595 (M + 1)⁺. Analysis: Found C, 57.28; H, 5.72; N, 13.51; C₂₉H₃₄N₆O₆S. 0.25CH₂Cl₂. requires C, 57.04; H, 5.65; N, 13.64%. |
| 6 | Propyl | Ethyl | 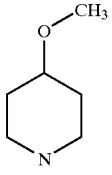 | B | δ (CDCl₃): 0.95 (3H, t), 1.30 (3H, t), 1.65–1.80 (2H, m), 1.80–2.00 (2H, m), 2.00–2.10 (2H, m), 3.00–3.10 (4H, m), 3.15–3.30 (6H, m), 4.20 (2H, t), 5.70 (2H, s), 7.10 (1H, d), 7.15 (1H, d), 7.20 (1H, m), 7.60 (1H, m), 7.80 (1H, m), 8.60 (1H, d), 8.80 (1H, s), 10.60 (1H, s). LRMS: m/z 567 (M + 1)⁺. Analysis: Found C, 58.60; H, 6.06; N, 14.47; C₂₈H₃₄N₆O₆S. 0.35H₂O requires C, 58.69; H, 6.10; N, 14.67%. |
| 7 | Propyl | Propyl | 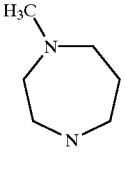 | A | δ (CDCl₃): 0.95 (3H, t), 1.15 (3H, t), 1.70–1.80 (2H, m), 1.90(2H, m), 2.00(2H, m), 2.35 (3H, s), 2.60–2.70 (4H, m), 3.00 (2H, t), 3.40–3.50 (4H, m), 4.20 (2H, t), 5.70 (2H, s), 7.05 (1H, d), 7.15 (1H, d), 7.20 (1H, m), 7.60 (1H, m), 7.85 (1H, m), 8.60 (1H, d), 8.80 (1H, s), 10.65 (1H, br s). LRMS: m/z 580 (M + 1)⁺. Analysis: Found C, 58.41; H, 6.52; N, 15.54; C₂₉H₃₇N₇O₄S. 0.2CH₂Cl₂.065CH₃OH, requires C, 58.06; H, 6.53 N, 15.88%. |
| 8 | Propyl | Propyl | 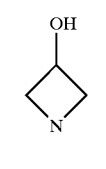 | B | δ (CDCl₃): 0.95 (3H, t), 1.15 (3H, t), 1.75 (2H, m), 2.00 (2H, m), 2.70 (1H, m), 3.00 (2H, m), 3.70 (2H, m), 4.10 (2H, m), 4.20 (2H, m), 4.50 (1H, s), 5.70 (2H, s), 7.10 (1H, d), 7.20 (1H, d), 7.25 (1H, m), 7.65 (1H, m), 7.90 (1H, m), 8.60 (1H, d), 8.80 (1H, s), 10.80 (1H, s). LRMS: m/z 539 (M + 1)⁺. Analysis: Found C, 57.75; H, 5.68; N, 15.52; C₂₆H₃₀N₆O₆S. requires C, 57.98; H, 5.61; N, 15.60%. |
| 9 | Propyl | Propyl | 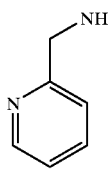 | A | δ (CDCl₃): 0.95 (3H, m), 1.15 (3H, m), 1.65–1.80 (2H, m), 1.95–2.10 (2H, m), 3.00 (2H, t), 4.20 (2H, t), 4.30 (2H, d), 5.70 (2H, s), 5.90 (1H, t), 7.00–7.30 (5H, m), 7.50–7.70 (2H, m), 7.90 (1H, m), 8.20 (1H, d), 8.60 (1H, d), 8.90 (1H, s), 10.60 (1H, s). LRMS: m/z 574 (M + 1)⁺. Analysis: Found C, 58.46; H, 5.29; N, 16.08; C₂₉H₃₁N₇O₄S. 0.5CH₂Cl₂. requires C, 58.85; H, 5.36; N, 16.56%. |
| 10 | Propyl | Propyl | 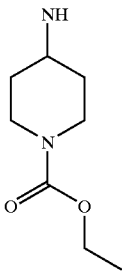 | A | δ (CDCl₃): 0.95 (3H, t), 1.15 (3H, t), 1.25 (3H, t), 1.30–1.45 (2H, m), 1.65–1.80 (2H, m), 1.80–1.90 (2H, m), 2.00–2.10 (2H, m), 2.80–2.95 (2H, t), 3.00 (2H, t), 3.40 (1H, m), 3.90–4.05 (2H, m), 4.10 (2H, m), 4.25 (2H, m), 4.60 (1H, d), 5.70 (2H, s), 7.10 (2H, m), 7.20 (1H, m), 7.60 (1H, m), 7.95 (1H, d), 8.60, (1H, d), 8.90 (1H, s), 10.65 (1H, s). LRMS: m/z 638 (M + 1)⁺. Analysis: Found C, 57.91; H, 6.26; N, 14.76; C₃₁H₃₉N₇O₆S. 0.4H₂O. 0.03CH₂Cl₂. requires C, 57.56; H, 6.20; N, 15.14%. |

-continued

| Example No. | R³ | R² | NR¹²R¹³ | Method | Data |
|---|---|---|---|---|---|
| 11 | Propyl | Propyl | 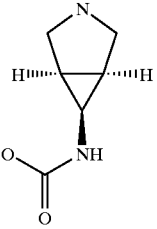 | A | δ (CDCl₃): 0.95 (3H, t), 1.15 (3H, t), 1.40 (9H, s), 1.60 (2H, m), 1.75 (2H, m), 2.00 (2H, m), 2.50 (1H, s), 3.00 (2H, m), 3.20 (2H, m), 3.65 (2H, m), 4.20 (2H, m) 4.60 (1H, br s), 5.70 (2H, m), 7.05 (1H, m), 7.15 (1H, m), 7.20 (1H, m), 7.60 (1H, m), 7.85 (1H, m), 8.60(1H, d), 8.80 (1H, s), 10.60 (1H, s). LRMS: m/z 664 (M + 1)⁺. Analysis: Found C, 58.43; H, 6.23; N, 14.11; C₃₂H₄₂N₇O₆S. 0.2H₂O. 0.6CH₃OH. requires C, 57.96; H, 6.68; N, 14.51%. |

Example 12

3-Ethyl-5-{5-[(3-ethylamino)-1-ethylaminosulfonyl]-2-n-propoxyphenyl}-2-(pyridin-2-yl)methyl-2,6-dihydro-7H-pyrazolo[4,3-d]pyrimidin-7-one The title compound of preparation 16 (0.5 g, 1.28 mmol) was added to a cooled mixture of chlorosulfonic acid (1 ml, 15 mmol) and thionyl chloride (0.15 ml, 2 mmol) and the reaction stirred for 4 hours, warming to room temperature. The reaction mixture was quenched by pouring onto ice and the white precipitate which formed was filtered and dried. The resultant solid was dissolved in a mixture of acetone (15 ml):water (10 ml), a solution of N-ethylethylenediamine (2 ml, 19 mmol) in acetone (5 ml) was added dropwise over 15 minutes, and the reaction mixture was stirred at room temperature for 45 minutes. The acetone was removed under reduced pressure and the aqueous residue was partitioned between dichloromethane (60 ml) and aqueous sodium hydroxide (1N, 30 ml). The layers were separated and the aqueous layer was neutralised by the addition of solid carbon dioxide. The aqueous layer was then extracted with dichloromethane (3×60 ml), the combined organic layers were dried over Na₂SO₄, filtered and concentrated under reduced pressure. The residue was purified by column chromatography on silica gel eluting with a gradient system of dichloromethane:methanol:0.88 ammonia (95:5:1 to 85:15:1) to afford the title compound as a white solid (200 mg).

δ(CDCl₃): 1.00 (3H,m), 1.15 (3H,m), 1.30 (3H,m), 1.95–2.10 (2H,m), 2.55 (2H,q), 2.75 (2H,m), 3.00–3.10 (4H,m), 4.25 (2H,t), 4.20 (2H,t), 5.70 (2H,s), 7.05–7.20 (2H,m), 7.20 (1H,m), 7.60 (1H,m), 7.95 (1H,m), 8.60 (1H, m), 8.90 (1H,s), 10.60 (1H,s).

LRMS: m/z 540 (M+1)⁺.

Example 13

5-[5-(N,N-Diethylaminosulfonyl)-2-n-propoxyphenyl]-3-ethyl-2-(pyridin-2-yl)methyl-2,6-dihydro-7H-pyrazolo[4,3-d]pyrimidin-7-one The title compound of preparation 16 (2.0 g, 5.13 mmol) was added slowly to chlorosulfonic acid (6 ml, 90 mmol) at 0° C. and stirred for 18 hours, warming to room temperature. The reaction mixture was quenched by pouring onto ice (40 g) and the resultant solution was basified to pH 9.0 by the addition of aqueous sodium hydroxide (5N), maintaining the temperature at 0° C. A solution of diethylamine (1.5 g, 20.5 mmol) in acetone (10 ml) was added and the reaction mixture stirred for 18 hours at room temperature. Water (10 ml) was added and the white precipitate was filtered, washed with acetone:water (1:1) and dried under vacuum at 50° C. to afford the title compound as a white solid (1.6 g).

δ(CDCl₃): 1.00–1.20 (9H,m), 1.30 (3H,t), 2.00 (2H,m), 3.00 (2H,q), 3.20–3.35 (4H,m), 4.20 (2H,t), 5.70 (2H,s), 7.10 (2H,t), 7.20 (1H,m), 7.60 (1H,m), 7.90 (1H,m), 8.60 (1H,d), 8.85 (1H,s), 10.60 (1H,s).

Example 14

5-[5-(3-N,N-Dimethylaminoazetidin-1-ylsulfonyl)-2-n-propoxyphenyl]-3-n-propyl-2-(pyridin-2-yl)methyl-2,6-dihydro-7H-pyrazolo[4,3-d]pyrimidin-7-one 10% Palladium on charcoal (560 mg) was added to a solution of N-(1-benzhydryl-3-azetidinyl)-N,N-dimethylamine (2.95 g, 11 mmol) in methanol (65 ml) under an atmosphere of nitrogen and stirred at room temperature. Ammonium formate (3.07 g, 48.7 mmol) was added and the reaction stirred under reflux for 5 hours. After cooling the mixture was filtered through a pad of ARBOCEL and washed with methanol. The solvent was removed from the filtrate under reduced pressure to give the crude solid N-(3-azetidinyl)-N,N-dimethylamine (1.76 g). The title compound of preparation 15 (0.82 g, 1.62 mmol) was dissolved in chlorosulfonic acid (2 ml, 30 mmol) and thionyl chloride (0.50 ml, 6.90 mmol) was added slowly. The resultant mixture was stirred at room temperature for 18 hours. The reaction mixture was quenched by pouring onto ice and the white precipitate which formed was filtered and dried under vacuum. The resultant solid was suspended in ethanol (5 ml), the previously prepared N-(3-azetidinyl)-N,N-dimethylamine (1.76 g) added and the mixture was stirred at room temperature for 18 hours. The solvent was removed under reduced pressure and the residue purified by column chromatography on silica gel eluting with a gradient system of dichloromethane:methanol (99:1 to 97:3) to afford the title compound as a white solid, (364 mg).

δ(CDCl₃): 0.95 (3H,t), 1.20 (3H,t), 1.65–1.80 (2H,m), 2.00–2.15 (8H,m), 3.00 (2H,m), 3.10 (1H,m) 3.60 (2H,m), 3.90 (2H,m), 4.30 (2H,m), 5.70 (2H,s), 7.10 (1H,d), 7.20–7.30 (2H,m), 7.65 (1H,m), 7.90 (1H,m), 8.60 (1H,d), 8.85 (1H,s), 10.65 (1H,s).

LRMS: m/z 566 (M+1)⁺.

Analysis: Found C, 58.09; H, 6.23; N, 16.85; C₂₈H₃₅N₇O₄S 0.75H₂O requires C, 58.07; H, 6.35; N, 16.93%.

Example 15

5-[2-Ethoxyphenyl-5-(2-pyrazinaminosulfonyl)]-3-ethyl-2-(pyridin-2-yl)methyl-2,6-dihydro-7H-pyrazolo[4,3-d]pyrimidin-7-one The title compound of preparation 23 (240 mg, 0.63 mmol) was added slowly to chlorosulfonic acid (1 ml, 15 mmol) and the reaction stirred for 18 hours at room temperature. The reaction mixture was quenched by pouring onto ice and a white precipitate was formed. The resultant mixture was neutralised by the addition of aqueous sodium hydroxide solution (5N) while the temperature was maintained at 0° C. The white precipitate was filtered off, washed with water, then diethyl ether and was dried under vacuum. 2-Aminopyrazine (126 mg, 1.32 mmol) was added to a suspension of sodium hydride (40 mg, 80% dispersion in mineral oil, 1.32 mmol) in tetrahydrofuran (3 ml) under an atmosphere of nitrogen at room temperature and stirred for 1 hour. The white solid previously obtained was added portion wise to this mixture over 2 minutes and stirred for 72 hours at room temperature. The reaction mixture was diluted with ethyl acetate (20 ml) and water (20 ml), the layers were separated and the aqueous layer acidified with hydrochloric acid (1N, 10 ml) and then extracted with ethyl acetate (40 ml×2). The latter organic phases were dried over $MgSO_4$, filtered and concentrated under reduced pressure. The residue was purified by column chromatography on silica gel eluting with a gradient system of dichloromethane:methanol (100:0 to 95:5) to afford the title compound as a white solid (30 mg).

$\delta(CDCl_3)$: 1.25 (3H,m), 1.60 (3H,t), 3.00 (2H,m), 4.30 (2H,m), 5.70 (2H,s), 7.10 (2H,m), 7.20 (1H,m), 7.60 (1H, m), 8.00 (1H,d), 8.20 (1H,s), 8.25 (1H,s), 8.60 (1H,s), 8.70 (1H,s), 8.90 (1H,s), 10.65 (1H,s).

LRMS: m/z 533 (M+1)$^+$.

Example 16

5-{5-[(3-Amino)-1-ethylaminosulfonyl]-2-n-propoxyphenyl}-3-n-propyl-2-(pyridin-2-yl)methyl-2,6-dihydro-7H-pyrazolo[4,3-d]pyrimidin-7-one dihydrochloride The title compound of preparation 29 (380 mg, 0.60 mmol) was dissolved in dichloromethane (5 ml) and saturated with hydrogen chloride gas whilst stirring at room temperature. Stirring continued for a further 2 hours then the solvent was removed under reduced pressure. The residue was azeotroped with dichloromethane and dried under vacuum to afford the title compound as a white solid (320 mg).

$\delta(d_6\text{-}DMSO)$: 0.80–1.00 (6H,m), 1.55–1.80 (4H,m), 2.80–3.00 (6H,m), 4.10 (2H,t), 5.70 (2H,s), 7.20–7.50 (3H, m), 7.85–7.95 (2H,m), 7.95–8.10 (4H,m), 8.60 (1H,d), 11.80 (1H,br s).

LRMS: m/z 526 (M+1)$^+$.

Analysis: Found C, 46.05; H, 5.66; N, 14.89; $C_{25}H_{31}N_7O_4S$ 2HCl 3$H_2O$ requires C, 46.01; H, 6.02; N, 15.02%.

Example 17

5-[5-(4-Oxo-piperidin-1-ylsulfonyl)-2-n-propoxyphenyl]-3-n-propyl-2-(pyridin-2-yl)methyl-2,6-dihydro-7H-pyrazolo[4,3-d]pyrimidin-7-one The title compound of example 5 (440 mg, 0.74 mmol) was dissolved in tetrahydrofuran (5 ml), hydrochloric acid (2N, 2.5 ml) was added dropwise, and the reaction stirred at room temperature for 1.5 hours, and warmed at 50° C. for a further 18 hours. The mixture was concentrated under reduced pressure and water (20 ml) was added to the residue. The resultant solution was neutralised by the addition of solid sodium hydrogencarbonate. The aqueous solution was extracted with ethyl acetate (40 ml), the organic layer was washed with brine (20 ml) and evaporated under reduced pressure. The residue was dissolved in dichloromethane and dried over $MgSO_4$, filtered and evaporated under reduced pressure to afford the title compound as a white solid, (358 mg).

$\delta(CDCl_3)$: 1.15 (3H,t), 1.30 (3H,t), 2.00 (2H,m), 2.55 (4H,m), 3.00 (2H,q), 3.45 (4H,m), 4.25 (2H,t), 5.70 (2H,s), 7.10 (1H,d), 7.20 (1H,d), 7.25 (1H,m), 7.60 (1H,m), 7.85 (1H,m), 8.60 (1H,d), 8.80 (1H,s), 10.60 (1H,s).

LRMS: m/z 551 (M+1)$^+$.

Analysis: Found C, 57.96; H, 5.44; N, 14.60; $C_{27}H_{30}N_6O_5S$ 0.6$H_2O$ requires C, 57.76; H, 5.60; N, 14.97%.

Example 18

5-{5-[(1R,5S,)-6-endo-Amino-3-azabicyclo[3.1.0] hex-3-ylsulfonyl]-2-n-propoxyphenyl}-3-n-propyl-2-(pyridin-2-yl)methyl-2,6-dihydro-7H-pyrazolo[4,3-d]pyrimidin-7-one The title compound of example 11 (320 mg, 0.48 mmol) was dissolved in dichloromethane (10 ml) and cooled to 0° C. Trifluoroacetic acid (2 ml) was added dropwise and the reaction mixture was stirred for 3 hours. The solvent was removed under reduced pressure and the residue was azeotroped with toluene, then dichloromethane. The residue was purified by column chromatography on silica gel eluting with a solvent system of dichloromethane:methanol:0.88 ammonia (95:5:1) to afford the title compound as a white solid (170 mg).

$\delta(CDCl_3)$: 0.95 (3H,t), 1.15 (3H,t), 1.45 (2H,s), 1.50 (2H,br s), 1.75 (2H,m), 2.00 (2H,m), 2.35 (1H,s), 2.95 (2H,t), 3.10 (2H,d), 3.60 (2H,d), 4.20 (2H,t), 5.70 (2H,s), 7.05 (1H,d), 7.15 (1H,d), 7.25 (1H,m), 7.60 (1H,m), 7.85 (1H,m), 8.60 (1H,d), 8.80 (1H,s), 10.60 (1H,br s).

LRMS: m/z 564 (M+1)$^+$.

Analysis: Found C, 57.91; H, 5.70; N, 16.70; $C_{28}H_{33}N_7O_4S$ 0.25$CH_2Cl_2$ requires C, 58.01; H, 5.77; N, 16.76%.

Example 19

5-[5-(N,N-Dimethylaminosulfonyl)-2-ethoxypyridin-3-yl]-3-n-propyl-2-(pyridin-2-yl) methyl-2,6dihydro-7H-pyrazolo[4,3-d]pyrimidin-7-one Potassium tert-butoxide (102 mg, 0.91 mmol) was added to a suspension of the title compound of preparation 43 (235 mg, 0.46 mmol) in ethanol (15 ml) and the reaction mixture heated in a sealed vessel at 100° C. and stirred for 18 hours. On cooling, the solvent was removed under reduced pressure and the residue was suspended in water (10 ml) and extracted with dichloromethane (2×10 ml). The combined organic layers were dried over $MgSO_4$, filtered and concentrated under reduced pressure. The residue was purified by column chromatography on silica gel eluting with a gradient system of dichloromethane:methanol (99:1 to 98:2) to afford the title compound as a brown foam (70 mg).

$\delta(CDCl_3)$: 0.95 (3H,t), 1.60 (3H,t), 1.70–1.85 (2H,m), 2.80 (6H,s), 3.00 (2H,t), 4.80 (2H,q), 5.70 (2H,s), 7.10 (1H,d), 7.20–7.30 (1H,m), 7.60 (1H,m), 8.60 (1H,m), 8.70 (1H,d), 9.05 (1H,s), 10.65 (1H,s).

LRMS: m/z 498 (M+1)$^+$.

Analysis: Found C, 55.30; H, 5.51; N, 18.87; $C_{23}H_{27}N_7O_4S$. 0.4$CH_3OH$. requires C, 55.07; H, 5.65; N, 19.21%.

Example 20

5-(5-[(3-N,N-Dimethylamino)-1-ethylaminosulfonyl]-2-n-propoxypyridin-3-yl)-3-n-propyl-2-(pyridin-2-yl)methyl-2,6-dihydro-7H-pyrazolo[4,3-d]pyrimidin-7-one A solution of the title compound of preparation 54 (130 mg, 0.3 mmol) in acetic acid (5 ml) and concentrated hydrochloric acid (5 ml) was cooled to −20° C. and sodium nitrite (42.8 mg, 0.62 mmol) added. The reaction mixture was warmed to 0° C. over 2 hours, then cooled back to −20° C. Sulfur dioxide (3 ml) was added followed by a suspension of copper(II) chloride (125 mg, 0.93 mmol) in water (1 ml) and acetic acid (2 ml). The reaction mixture was warmed to 0° C., stirred for 30 minutes, then warmed to room temperature and stirred for 2 hours. The reaction mixture was poured onto ice (10 g) and extracted with dichloromethane (3×20 ml). The combined organic layers were dried over $MgSO_4$, filtered, concentrated under reduced pressure and the residue was azeotroped with toluene. The resultant green solid was dissolved in ethanol (5 ml), N,N-dimethylethylenediamine (0.068 ml, 0.62 mmol) was added and the reaction stirred at room temperature for 18 hours. The solvent was removed under reduced pressure and the residue purified by column chromatography on silica gel eluting with a gradient system of dichloromethane:methanol (97:3 to 95:5). This product was suspended in pentane and filtered to afford the title compound as a yellow solid (90 mg).

$\delta(d_6$-DMSO): 0.85 (3H,t), 0.95 (3H,t), 1.60–1.80 (4H,m), 2.05 (6H,s), 2.30 (2H,t), 2.90 (4H,m), 4.20 (2H,t), 5.70 (2H,s), 7.20 (1H,d), 7.30 (1H,m), 7.80 (1H,m), 8.30 (1H,d), 8.50 (1H,d), 8.65 (1H,s), 11.80 (1H,br s).

LRMS: m/z 555 (M+1)$^+$.

Analysis: Found C, 53.73; H, 6.09; N, 18.58; $C_{26}H_{34}N_8O_4S$ 0.5$CH_2Cl_2$ requires C, 53.30; H, 5.91; N, 18.77%.

Example 21

3-Ethyl-5-{[5-(3-ethylamino)-1-ethylaminosulfonyl]-2-[2-methoxyethoxy]pyridin-3-yl}-2-(pyridin-2-yl)methyl-2,6dihydro-7H-pyrazolo[4,3-d]pyrimidin-7-one A solution of the title compound of preparation 56 (150 mg, 0.30 mmol) in dichloromethane (10 ml) was added over 1 hour, to a solution of N-ethylethylenediamine (125 μl, 1.20 mmol) and triethylamine (166 μl, 1.20 mmol) in dichloromethane (10 ml) and stirred at room temperature for a further hour. The reaction mixture was washed with water (10 ml), dried over $MgSO_4$, filtered and concentrated under reduced pressure. The residue was purified by column chromatography on silica gel eluting with a solvent system of dichloromethane:methanol: 0.88 ammonia (97:3:0.3) to afford the title compound as a white solid (40 mg).

$\delta(CDCl_3)$: 1.00 (3H,t), 1.30 (3H,t), 2.50 (2H,m), 2.70 (2H,t), 3.00 (4H,m), 3.60 (3H,s), 3.85 (2H,t), 4.80 (2H,t), 5.70 (2H,s), 7.10 (1H,d), 7.20 (1H,m), 7.60 (1H,m), 8.60 (1H,d), 8.70 (1H,d), 9.05 (1H,s).

LRMS: m/z 557 (M+1)$^+$.

Analysis: Found C, 53.60; H, 5.76; N, 19.84; $C_{25}H_{32}N_8O_5S$ requires C, 53.94; H, 5.79; N, 20.13%.

Example 22

3-Ethyl-5-[5-(4-ethylpiperidin-1-ylsulfonyl)-2-(2-methoxymethyl)pyridin-3-yl]-2-(pyridin-2-yl)methyl-2,6-dihydro-7H-pyrazolo[4,3-d]pyrimidin-7-one Obtained from the title compound of preparation 56 and 4-ethylpiperidine using an analogous method to example 21, as a white solid (20%).

$\delta(CDCl_3)$: 0.85 (3H,t), 1.10 (1H,m), 1.20–1.40 (7H,m), 1.80 (2H,m), 2.35 (2H,t), 3.00–3.10 (2H,m), 3.60 (3H,s), 3.80–3.90 (4H,m), 4.80 (2H,m), 5.70 (2H,s), 7.10 (1H,d), 7.20 (1H,m), 7.60 (1H,m), 8.75 (1H,m), 8.60 (1H,s), 9.00 (1H, s), 10.85 (1H,s).

LRMS: m/z 582 (M+1)$^+$.

Example 23

3-Ethyl-5-[2-(2-methoxymethyl)-5-(tetrahydro-1,4-thiazine 1,1-dioxide sulfonyl)pyridin-3-yl]-2-(pyridin-2-yl)methyl-2,6-dihydro-7H-pyrazolo[4,3-d]pyrimidin-7-one Obtained from the title compound of preparation 56 and the title compound of preparation 58 using an analogous method to example 21, as a white solid (13%).

$\delta(CDCl_3)$: 1.30 (3H,t), 3.00–3.10 (2H,m), 3.20 (4H,m), 3.60 (3H,s), 3.80 (4H,m), 3.90 (2H,m), 4.80 (2H,m), 5.70 (2H,s), 7.10 (1H,d), 7.30 (1H,m), 7.70 (1H,m), 8.60 (1H,d), 8.65 (1H,s), 9.00 (1H,s), 10.80 (1H,s).

LRMS: m/z 604 (M+1)$^+$.

Example 24

5-{2-Ethoxy-5-[(3-N-ethylamino)-1-azetindinesulfonyl]pyridin-3-yl}-3-n-propyl-2-(pyridin-2-yl)methyl-2,6-dihydro-7H-pyrazolo[4,3-d]pyrimidin-7-one Water (10 ml) was added to a solution of the tide compound of preparation 59 (420 mg, 0.65 mmol) in methanol (10 ml). A solution of saturated sodium carbonate (5 ml) was added and the reaction mixture was stirred at room temperature for 18 hours. The methanol was removed under reduced pressure and further water (30 ml) was added. The aqueous layer was extracted with ethyl acetate (3×30 ml), the combined organic layers were washed with brine (3×30 ml), dried over $MgSO_4$, filtered and concentrated under reduced pressure. The residue was purified by column chromatography on silica gel eluting with a gradient system of dichloromethane:methanol (100:0 to 97.5:2.5) to afford an oil. This oil was dissolved in diethyl ether and concentrated under reduced pressure (repeated ×3), then recrystallised from ethyl acetate:hexane to afford the title compound as colourless crystals (185 mg).

$\delta(CDCl_3)$: 0.95 (3H,t), 1.05 (3H,t), 1.60 (3H,t), 1.65–1.80 (2H,m), 2.50–2.60 (2H,m), 3.00 (2H,t), 3.60 (3H,m), 4.00–4.10 (2H,m), 4.80 (2H,q), 5.70 (2H,s), 7.10 (1H,d), 7.20 (1H,m), 7.60 (1H,m), 8.60 (1H,d), 8.70 (1H,s), 9.10 (1H,s), 10.65 (1H,s).

LRMS: m/z 553 (M+1)$^+$.

Analysis: Found C, 56.41; H, 5.83; N, 20.19; $C_{26}H_{32}N_8O_4S$ requires C, 56.51; H, 5.84; N, 20.28%.

Example 25

5-{5-[(1R,5S)-6-exo-Amino-3-azabicyclo[3.1.0]hex-3-yl sulfonyl]-2-ethoxy-pyridin-3-yl}-3-n-propyl-2-(pyridin-2-yl)methy2,6-dihydro-7H-pyrazolo[4,3-d]pyrimidin-7-one The title compound of preparation 60 (300 mg, 0.46 mmol) was dissolved in ethyl acetate (40 ml) and hydrogen chloride gas was bubbled through for 20 minutes, whilst stirring at 0° C. The solvent was removed under reduced pressure and the residue azeotroped with diethyl ether. The solid was dissolved in water (50 ml) and basified with saturated sodium carbonate solution. The aqueous solution was then extracted with ethyl acetate (3×30 ml), and the combined organic layers were washed with brine (3×20 ml), dried over $Na_2SO_4$, filtered and concentrated under reduced pressure. The residue was dissolved in diethyl ether and concentrated under reduced pressure (repeated ×3), then recrystallised from ethyl acetate:hexane to afford the title compound as colourless solid (145 mg).

δ($CDCl_3$): 0.95 (3H,t), 1.40–1.65 (7H,m), 1.65–1.80 (2H,m), 2.40 (1H,s), 3.00 (2H,t), 3.10 (2H,d) 3.60 (2H,d), 4.70–4.80 (2H,q), 5.70 (2H,s), 7.10 (1H,d), 7.20–7.25 (1H,m), 7.60 (1H,m), 8.60 (1H,d), 8.65 (1H,s), 9.05 (1H,s), 10.65 (1H,s).

LRMS: m/z 551 $(M+1)^+$.

Analysis: Found C, 56.18; H, 5.53; N, 19.84; $C_{26}H_{30}N_8O_4S$ $0.5H_2O$ requires C, 55.80; H, 5.58; N, 20.02%.

BIOLOGICAL ACTIVITY

Compounds of the invention were found to have in vitro activities as inhibitors of cGMP PDE5 with $IC_{50}$ values of less than about 100 nM.

The following Table illustrates the in vitro activities for a range of compounds of the invention as inhibitors of cGMP PDE5.

| Example | $IC_{50}$ (nM) |
|---------|----------------|
| 4       | 26.60          |
| 8       | 16.40          |
| 10      | 14.00          |
| 19      | 9.70           |
| 20      | 8.50           |
| 22      | 10.30          |

What is claimed is:
1. A compound of formula IA, or of formula IB:

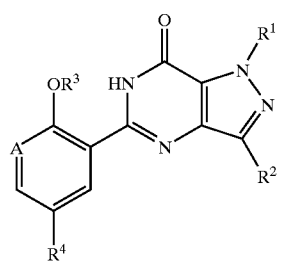

IA

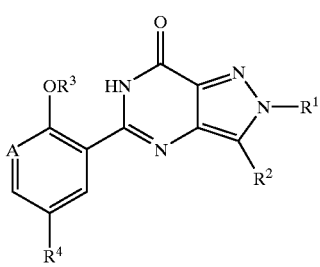

IB wherein
A represents CH or N;
$R^1$ represents $Het^1$, $Het^1$alkyl, aryl or arylalkyl, all of which are optionally substituted by one or more substituents selected from halo, cyano, nitro, lower alkyl, lower alkenyl, lower alkynyl, cyclic lower alkyl, or part cyclic/acyclic lower alkyl, $OR^5$, $C(O)R^6$, $C(O)OR^7$, $C(O)NR^8R^9$, $NR^{10a}R^{10b}$ and $SO_2NR^{11a}R^{11b}$;

$R^2$ and $R^3$ independently represent H, lower alkyl, lower alkenyl, lower alkynyl, cyclic lower alkyl, or part cyclic/acyclic lower alkyl which latter group is optionally substituted by one or more substituents selected from aryl, $Het^1$, halo, cyano, nitro, $OR^5$, $C(O)R^6$, $C(O)OR^7$, $C(O)NR^8R^9$, $NR^{10a}R^{10b}$ and $SO_2NR^{11a}R^{11b}$;

$R^4$ represents $SO_2NR^{12}R^{13}$;

$R^{12}$ and $R^{13}$ independently represent H, lower alkyl, lower alkenyl, lower alkynyl, cyclic lower alkyl, or part cyclic/acyclic lower alkyl optionally substituted by one or more substituents selected from aryl, $Het^1$, halo, cyano, nitro, lower alkyl, lower alkenyl, lower alkynyl, cyclic lower alkyl, or part cyclic/acyclic lower alkyl, $OR^5$, $C(O)R^6$, $C(O)OR^7$, $C(O)NR^8R^9$, $NR^{10}R^{10a}$ and $SO_2NR^{11a}R^{11b}$; $Het^1$; or together with the nitrogen to which they are attached, form $Het^2$ or a structural fragment of formula IIa:

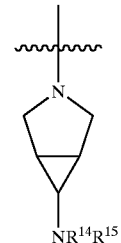

IIa $R^{14}$ and $R^{15}$ independently represent H, lower alkyl, lower alkenyl, lower alkynyl, cyclic lower alkyl, part cyclic/acyclic lower alkyl, $C(O)R^6$, $C(O)OR^7$ or $C(O)NR^8R^9$;

$Het^1$ represents an optionally substituted four- to twelve-membered heterocyclic group, which group contains at least one nitrogen atom and, optionally, one or more further heteroatoms selected from nitrogen, oxygen and sulphur;

$Het^2$ represents an optionally substituted three- to twelve-membered heterocyclic group, which group contains at least one nitrogen atom and, optionally, one or more further heteroatoms selected from nitrogen, oxygen and sulphur; and $R^5$, $R^6$, $R^7$, $R^8$, $R^9$, $R^{10a}$, $R^{10b}$, $R^{11a}$ and $R^{11b}$ independently represent H, lower alkyl, lower alkenyl, lower alkynyl, cyclic lower alkyl, part cyclic/acyclic lower alkyl;

or a pharmaceutically, or a veterinarily, acceptable salt or solvate thereof;

provided that when $R^2$ represents $C_{1-6}$ alkyl and:
(a) A represents CH; $R^1$ represents $Het^1$ or $CH_2Het^1$ (in which both cases $Het^1$ represents a C-linked 6-membered heterocyclic group containing one or two nitrogen atoms, optionally in the form of its mono-N-oxide, or a C-linked 5-membered heterocyclic group containing from one to four heteroatoms selected from nitrogen, oxygen and sulphur, wherein either of said heterocyclic groups is optionally substituted with one or two substituents selected from $C_{1-4}$ alkyl, which alkyl group is optionally substituted with $C_{1-4}$ alkoxy, halo or $NH_2$), phenyl or benzyl (which latter two groups are optionally substituted with one or two substituents selected from $C_{1-4}$ alkyl, $C_{1-4}$ alkoxy, halo, CN, $CONH_2$, $NO_2$, $NH_2$ and $S_2NH_2$); and $R^3$ is $C_{1-6}$ alkyl optionally substituted with $C_{1-4}$ alkoxy; then $R^{12}$ and $R^{13}$ do not represent, together with the nitrogen atom to which they are attached, a piperazinyl group, optionally substituted in the 4(N) position with $C_{1-4}$ alkyl optionally substituted with OH, $C_{1-4}$ alkoxy or $CONH_2$; and (b) A represents N; $R^1$ represents $CH_2Het^1$ (in which $Het^1$ represents a C-linked 6-membered heterocyclic group containing one or two nitrogen atoms, optionally in the form of its mono-N-oxide, or a C-linked 5-membered heterocyclic group containing two or three nitrogen atoms, wherein either of said heterocyclic groups is optionally substituted with $C_{1-4}$ alkyl) or benzyl; and $R^3$ is $C_{1-4}$ alkyl (optionally substituted with one or two substituents selected from OH, $C_{1-4}$ alkoxy, benzyloxy, $NR^{5a}R^{6a}$ (where $R^{5a}$ and $R^{6a}$ are each independently selected from H and $C_{1-4}$ alkyl or, together with the nitrogen atom to which they are attached, form a pyrrollidinyl, piperidinyl or morpholinyl group), phenyl, furanyl or pyridinyl), $C_{3-6}$ cycloalkyl or 1-($C_{1-4}$alkyl) piperidinyl; then $R^{12}$ and $R^{13}$ do not represent, together with the nitrogen atom to which they are attached, a 4-piperazinyl group, optionally substituted with one or two $C_{1-4}$ alkyl groups, optionally in the form of its 4-N-oxide, and optionally substituted at the 4(N) position with $C_{1-4}$ alkyl optionally substituted with one or two substituents selected from OH, $NR^{5a}R^{6a}$, $CONR^{5a}R^{6a}$ (in which both cases $R^{5a}$ and $R^{6a}$ are as defined above).

2. A compound as claimed in claim 1 wherein $R^1$ represents $Het^1C_{1-6}$alkyl, in which $Het^1$ represents a six-membered aromatic heterocyclic group containing one or more nitrogens.

3. A compound as claimed in claim 1, wherein $R^2$ represents linear, branched, cyclic, or acyclic lower alkyl.

4. A compound as claimed in claim 1, wherein $R^3$ represents linear, branched, cyclic, or acyclic lower alkyl, which is optionally substituted or terminated by $OR^5$ (in which $R^5$ is H or linear, branched, or cyclic $C_1$–$C_3$ alkyl).

5. A compound as claimed in any one of the preceding claims, wherein $R^{12}$ and $R^{13}$ independently represent H; linear, branched cyclic or acyclic lower alkyl, which alkyl group is optionally substituted and/or terminated by one or more substituents selected from $OR^5$ (in which $R^5$ is H or linear, branched, or cyclic $C_1$–$C_3$ alkyl), $Het^1$ (where $Het^1$ represents a six-membered aromatic heterocyclic group containing one or more nitrogens), or $NR^{10}R^{11}$; $Het^1$ (where $Het^1$ represents a six-membered heterocyclic group containing one or two nitrogens); or, together with the nitrogen atom to which they are attached, represent morpholinyl, tetrahydrothiazinyl, aza- or diazacyclo-($C_3$–$C_8$)-alkyl (which latter groups are all optionally substituted by one or more substituents selected from oxo, ethyleneketal, $OR^5$ (in which $R^5$ is H or linear, branched, or cyclic $C_1$–$C_3$ alkyl), $NR^{10}R^{11}$ or lower alkyl, lower alkenyl, lower alkynyl, cyclic lower alkyl, part cyclic/acyclic lower alkyl), or a structural fragment of formula IIa as defined in claim 1, in which $R^{14}$ and $R^{15}$ independently represent H, linear, branched, cyclic, or acyclic $C_1$–$C_3$ alkyl or $C(O)OR^7$, where $R^7$ represents linear or branched $C_1$–$C_4$ alkyl.

6. A formulation comprising a compound as defined in claim 1 in admixture with a pharmaceutically or veterinarily acceptable adjuvant, diluent or carrier.

7. A formulation as claimed in claim 6, which is a pharmaceutical formulation.

8. A formulation as claimed in claim 6, which is a veterinary formulation.

9. A method of treating or preventing a medical condition, wherein the condition is male erectile dysfunction, female sexual dysfunction, premature labour, dsymenorrhoea, benign prostatic hyperplasia (BPH), bladder outlet obstruction, incontinence, stable or unstable variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, a disease characterised by disorders of gut motility, pre-eclampsia, Kawasaki's syndrome, nitrate tolerance, peripheral diabetic neuropathy, stroke, acute respiratory failure, or skin necrosis, which comprises administering a therapeutically effective amount of a compound as claimed in claim 1 to a patient in need of such treatment.

10. A process for the preparation of a compound of formula IA, or of formula IB, as defined in claim 1, which comprises:

(a) reaction of a corresponding compound of formula IIIA, or of formula IIIB, respectively:

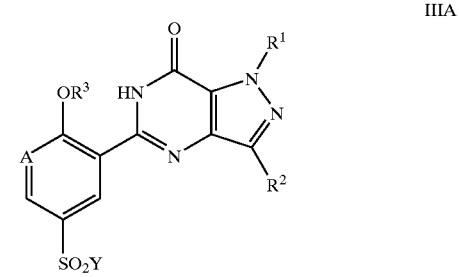

IIIA

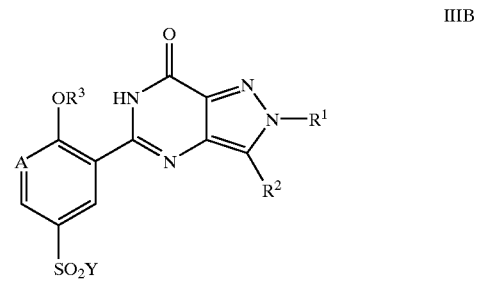

IIIB n Y is a leaving group and $R^1$, $R^2$, $R^3$ and A are as defined in claim 1, with a compound of formula IV:

$$R^{12}R^{13}NH \qquad\qquad IV$$

wherein $R^{12}$ and $R^{13}$ are as defined in claim 1;

(b) cyclisation of a corresponding compound of formula XVIA, or of formula XVIB, respectively:

XVIA

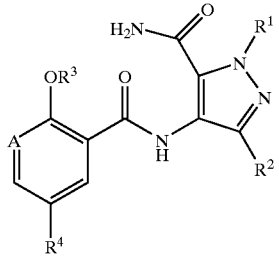

XVIB

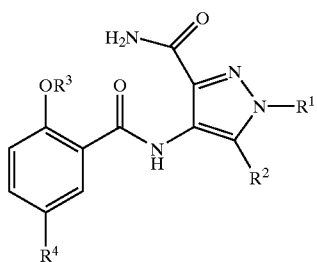

wherein $R^1$, $R^2$, $R^3$, $R^4$ and A are as defined in claim 1;

(c) for compounds of formulae IA and IB in which $R^1$ represents Het$^1$alkyl or arylalky, alkylation of a corresponding compound of formula XVIIIA, or of formula XVIIIB, respectively:

XVIIIA

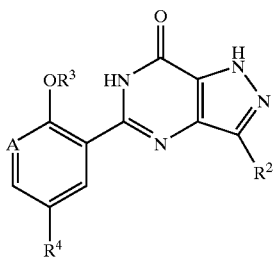

XVIIIB

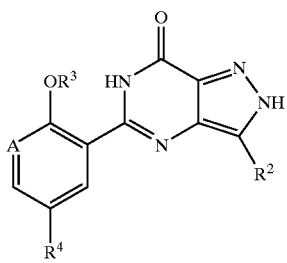

wherein $R^2$, $R^3$, $R^4$ and A are as defined in claim 1;

(e) conversion of one $R^3$ group to another by alkoxide exchange;

(f) for compounds of formula IA or IB in which $R^{12}$ and $R^{13}$, together with the nitrogen to which they are attached, form a N-alkyldiazacyclo-($C_3$–$C_{12}$)-alkyl group, alkylation of a corresponding compound of formula IA or IB in which $R^{12}$ and $R^3$, together with the nitrogen to which they are attached, form a diazacyclo-($C_3$–$C_{12}$)-alkyl group; or (g) deprotection of a protected derivative of a compound of formula IA or of formula IB.

11. A compound of formula IIIA, or of formula IIIB, as defined in claim 10.

12. A compound of formula XVIA, or of formula XVIB, as defined in claim 10.

13. A compound of formula XVIIIA, or of formula XVIIIB, as defined in claim 10.

* * * * *